United States Patent
Sullivan

(10) Patent No.: US 12,179,031 B2
(45) Date of Patent: Dec. 31, 2024

(54) HEART RATE CALCULATOR WITH REDUCED OVERCOUNTING

(71) Applicant: WEST AFFUM HOLDINGS DAC, Dublin (IE)

(72) Inventor: Joseph L. Sullivan, Kirkland, WA (US)

(73) Assignee: West Affum Holdings DAC, Dublin (IE)

( * ) Notice: Subject to any disclaimer, the term of this patent is extended or adjusted under 35 U.S.C. 154(b) by 0 days.

(21) Appl. No.: 17/843,584

(22) Filed: Jun. 17, 2022

(65) Prior Publication Data
US 2022/0314011 A1    Oct. 6, 2022

Related U.S. Application Data

(62) Division of application No. 16/140,324, filed on Sep. 24, 2018, now Pat. No. 11,364,387.
(Continued)

(51) Int. Cl.
*A61N 1/39* (2006.01)
*A61B 5/349* (2021.01)
(Continued)

(52) U.S. Cl.
CPC ............ *A61N 1/3904* (2017.08); *A61B 5/349* (2021.01); *A61N 1/046* (2013.01); *A61N 1/0484* (2013.01);
(Continued)

(58) Field of Classification Search
CPC .... A61N 1/3904; A61N 1/046; A61N 1/0484; A61N 1/3925; A61N 1/3968;
(Continued)

(56) References Cited

U.S. PATENT DOCUMENTS

| | | |
|---|---|---|
| 3,724,355 A | 4/1973 | Unger |
| 4,583,524 A | 4/1986 | Hutchins |
| (Continued) | | |

FOREIGN PATENT DOCUMENTS

| | | |
|---|---|---|
| WO | 1998039061 A2 | 9/1998 |
| WO | 2012064604 A1 | 5/2012 |

OTHER PUBLICATIONS

Heartstart MRx and XL AED Algorithm—Application Note, Jul. 2001, Edition 2, Philips Healthcare, USA, 10 pages.
(Continued)

*Primary Examiner* — Tammie K Marlen
*Assistant Examiner* — Maria Catherine Anthony
(74) *Attorney, Agent, or Firm* — Polsinelli PC

(57) ABSTRACT

A heart rate (HR) monitor for use in a medical device configurable to measure a patient's ECG such as, for example, a WCD system. Embodiments can include an ECG sensor and a processor configured with classification criteria to classify a received ECG signal into one of a plurality of ECG rhythm types each with a corresponding algorithm to determine the patient's heart rate. The processor uses the classification criteria to identify the ECG signal's type and determine a heart rate of the patient using the corresponding algorithm. The HR monitor is configurable to avoid overcounting of erroneous measurements of R-R intervals that can result from large T-waves and/or bigeminy by comparing the mean of even R-R intervals with the mean of odd R-R intervals. If the means are significantly different double counting or bigeminy is indicated and the HR calculation is adjusted accordingly.

18 Claims, 8 Drawing Sheets

ILLUSTRATIVE WEARABLE CARDIOVERTER DEFIBRILLATOR (WCD) SYSTEM

Related U.S. Application Data

(60) Provisional application No. 62/538,172, filed on Jul. 28, 2017.

(51) Int. Cl.
*A61N 1/04* (2006.01)
*A61B 5/00* (2006.01)
*A61B 5/0205* (2006.01)

(52) U.S. Cl.
CPC .......... *A61B 5/0205* (2013.01); *A61B 5/6805* (2013.01); *A61N 1/3925* (2013.01); *A61N 1/3968* (2013.01); *A61N 1/3993* (2013.01)

(58) Field of Classification Search
CPC .... A61N 1/3993; A61B 5/349; A61B 5/0205; A61B 5/6805; A61B 5/0006; A61B 5/02416; A61B 5/0022
See application file for complete search history.

(56) References Cited

U.S. PATENT DOCUMENTS

| | | | |
|---|---|---|---|
| 4,619,265 A | 10/1986 | Morgan et al. | |
| 4,928,690 A | 5/1990 | Heilman et al. | |
| 4,955,381 A | 9/1990 | Way et al. | |
| 5,078,134 A | 1/1992 | Heilman et al. | |
| 5,228,449 A | 7/1993 | Christ et al. | |
| 5,313,953 A * | 5/1994 | Yomtov | A61B 5/0031 600/517 |
| 5,353,793 A | 10/1994 | Bomn | |
| RE34,800 E | 11/1994 | Hutchins | |
| 5,394,892 A | 3/1995 | Kenny | |
| 5,405,362 A | 4/1995 | Kramer et al. | |
| 5,474,574 A | 12/1995 | Payne et al. | |
| 5,662,690 A | 9/1997 | Cole et al. | |
| 5,782,878 A | 7/1998 | Morgan et al. | |
| 5,792,204 A | 8/1998 | Snell | |
| 5,902,249 A | 5/1999 | Lysler | |
| 5,913,685 A | 6/1999 | Hutchins | |
| 5,944,669 A | 8/1999 | Kalb | |
| 6,047,203 A | 4/2000 | Sackner et al. | |
| 6,065,154 A | 5/2000 | Hulings et al. | |
| 6,108,197 A | 8/2000 | Janik | |
| 6,148,233 A | 11/2000 | Owen et al. | |
| 6,201,992 B1 | 3/2001 | Freeman | |
| 6,263,238 B1 | 7/2001 | Brewer et al. | |
| 6,287,328 B1 | 9/2001 | Snyder et al. | |
| 6,304,780 B1 | 10/2001 | Owen et al. | |
| 6,319,011 B1 | 11/2001 | Motti et al. | |
| 6,334,070 B1 | 12/2001 | Nova et al. | |
| 6,356,785 B1 | 3/2002 | Snyder | |
| 6,437,083 B1 | 7/2002 | Owen et al. | |
| 6,529,875 B1 | 3/2003 | Nakajima | |
| 6,546,285 B1 | 4/2003 | Owen et al. | |
| 6,681,003 B2 | 1/2004 | Linder et al. | |
| 6,762,917 B1 | 7/2004 | Verbiest et al. | |
| 6,871,089 B2 | 3/2005 | Korzinov | |
| 7,065,401 B2 | 6/2006 | Worden | |
| 7,559,902 B2 | 7/2009 | Ting et al. | |
| 7,610,090 B1 * | 10/2009 | Hofstadter | A61N 1/3702 600/509 |
| 7,865,238 B2 | 1/2011 | Brink | |
| 7,870,761 B2 | 1/2011 | Valentine et al. | |
| 7,974,689 B2 | 7/2011 | Volpe et al. | |
| 8,135,462 B2 | 3/2012 | Owen et al. | |
| 8,140,154 B2 | 10/2012 | Donnelly et al. | |
| 8,369,944 B2 | 2/2013 | Macho et al. | |
| 8,644,925 B2 | 2/2014 | Volpe et al. | |
| 8,676,313 B2 | 3/2014 | Volpe et al. | |
| 8,897,860 B2 | 11/2014 | Volpe et al. | |
| 8,965,500 B2 | 2/2015 | Macho et al. | |
| 9,008,801 B2 | 4/2015 | Kaib et al. | |
| 9,131,901 B2 | 9/2015 | Volpe et al. | |
| 9,132,267 B2 | 9/2015 | Kaib | |
| 9,345,898 B2 | 5/2016 | Piha et al. | |
| 9,408,548 B2 | 8/2016 | Volpe et al. | |
| 9,878,171 B2 | 1/2018 | Kaib | |
| 9,901,741 B2 | 2/2018 | Chapman et al. | |
| 10,016,613 B2 | 7/2018 | Kavounas | |
| 2002/0181680 A1 | 12/2002 | Linder et al. | |
| 2003/0120164 A1 | 6/2003 | Nielsen | |
| 2003/0158593 A1 | 8/2003 | Heilman et al. | |
| 2003/0176795 A1 * | 9/2003 | Harris | A61B 5/7285 600/485 |
| 2005/0107833 A1 | 5/2005 | Freeman et al. | |
| 2005/0107834 A1 | 5/2005 | Freeman et al. | |
| 2006/0173499 A1 | 8/2006 | Hampton et al. | |
| 2008/0312709 A1 | 12/2008 | Volpe et al. | |
| 2009/0005827 A1 | 1/2009 | Weintraub et al. | |
| 2009/0275849 A1 | 11/2009 | Stewart | |
| 2010/0007413 A1 | 1/2010 | Herleikson | |
| 2010/0298899 A1 | 11/2010 | Donnelly et al. | |
| 2011/0022105 A9 | 1/2011 | Owen et al. | |
| 2011/0288604 A1 | 11/2011 | Kaib et al. | |
| 2011/0288605 A1 | 11/2011 | Kaib et al. | |
| 2012/0112903 A1 | 5/2012 | Kaib et al. | |
| 2012/0144551 A1 | 6/2012 | Guldalian | |
| 2012/0150008 A1 | 6/2012 | Kaib et al. | |
| 2012/0158075 A1 | 6/2012 | Kaib et al. | |
| 2012/0191476 A1 | 7/2012 | Reid et al. | |
| 2012/0265265 A1 | 10/2012 | Razavi et al. | |
| 2012/0271185 A1 | 10/2012 | Sanghera et al. | |
| 2012/0283794 A1 | 11/2012 | Kaib et al. | |
| 2012/0302860 A1 | 11/2012 | Volpe et al. | |
| 2013/0012830 A1 | 1/2013 | Leininger et al. | |
| 2013/0085538 A1 | 4/2013 | Volpe et al. | |
| 2013/0144355 A1 | 6/2013 | Macho et al. | |
| 2013/0231711 A1 | 9/2013 | Kaib | |
| 2013/0245388 A1 | 9/2013 | Rafferty et al. | |
| 2013/0274565 A1 | 10/2013 | Langer et al. | |
| 2013/0317852 A1 | 11/2013 | Worrell et al. | |
| 2013/0325078 A1 | 12/2013 | Whiting et al. | |
| 2014/0012144 A1 | 1/2014 | Crone | |
| 2014/0025131 A1 | 1/2014 | Sullivan et al. | |
| 2014/0046391 A1 | 2/2014 | Cowan et al. | |
| 2014/0070957 A1 | 3/2014 | Longinotti-Buritonil et al. | |
| 2014/0324112 A1 | 10/2014 | Macho et al. | |
| 2014/0378812 A1 | 12/2014 | Saroka et al. | |
| 2015/0039053 A1 | 2/2015 | Kaib et al. | |
| 2015/0164349 A1 * | 6/2015 | Gopalakrishnan | A61B 5/746 600/508 |
| 2016/0004831 A1 | 1/2016 | Carlson et al. | |
| 2016/0067514 A1 | 3/2016 | Sullivan | |
| 2016/0106991 A1 | 4/2016 | Stadler et al. | |
| 2016/0114169 A1 | 4/2016 | Sheldon et al. | |
| 2016/0283900 A1 | 9/2016 | Johnson et al. | |
| 2017/0128735 A1 * | 5/2017 | Gustavson | A61B 5/6805 |
| 2017/0238814 A1 | 8/2017 | Gopalakrishnan et al. | |
| 2017/0319862 A1 | 11/2017 | Foshee, Jr. et al. | |
| 2017/0367591 A1 | 12/2017 | Jorgenseon | |
| 2018/0184933 A1 | 7/2018 | Sullivan et al. | |
| 2018/0185662 A1 | 7/2018 | Foshee, Jr. et al. | |
| 2018/0243578 A1 | 8/2018 | Volosin | |
| 2019/0030352 A1 | 1/2019 | Sullivan et al. | |
| 2019/0076666 A1 | 3/2019 | Medema | |

OTHER PUBLICATIONS

Klein, H. U., Goldenberg I., & Moss, A. J., Risk Stratification for Implantable Cardioverter Defibrillator Therapy: The Role of the Wearable Cardioverter-Defibrillator, Clinical update, European Heart Jounal, May 31, 2013, pp. 1-14, doi:10.1093/eurheartj/eht167, European Society of Cardiology.

Langendorf, R., et al., "Mechanisms of Intermittent Ventricular Bigeminy: I. Appearance of Ectopic Beats Dependent Upon Length of the Ventricular Cycle, the 'Rule of Bigeminy,'" Circulation 11:422-430, Mar. 1955.

Lifecor LifeVest System Model WCD 3100 Operator's Manual, 2006, PN 20B0040 Rev FI, Zoll Lifecor Corporation, Pittsburgh, PA.

(56) References Cited

OTHER PUBLICATIONS

The LifeVest Network/Patient Data Management System, Zoll, 2015, 20C0503 Rev A, 4 pages.
Zoll LifeVest Model 4000 Patient Manual PN 20B0047 Rev B, (C) 2009-2012; 108 pages.

* cited by examiner

ILLUSTRATIVE WEARABLE CARDIOVERTER DEFIBRILLATOR (WCD) SYSTEM

ILLUSTRATIVE COMPONENTS OF EXTERNAL DEFIBRILLATOR

SOME COMPONENTS OF A HEART RATE CALCULATOR WITH REDUCED OVERCOUNTING OF AN ILLUSTRATIVE EXTERNAL DEFIBRILLATOR

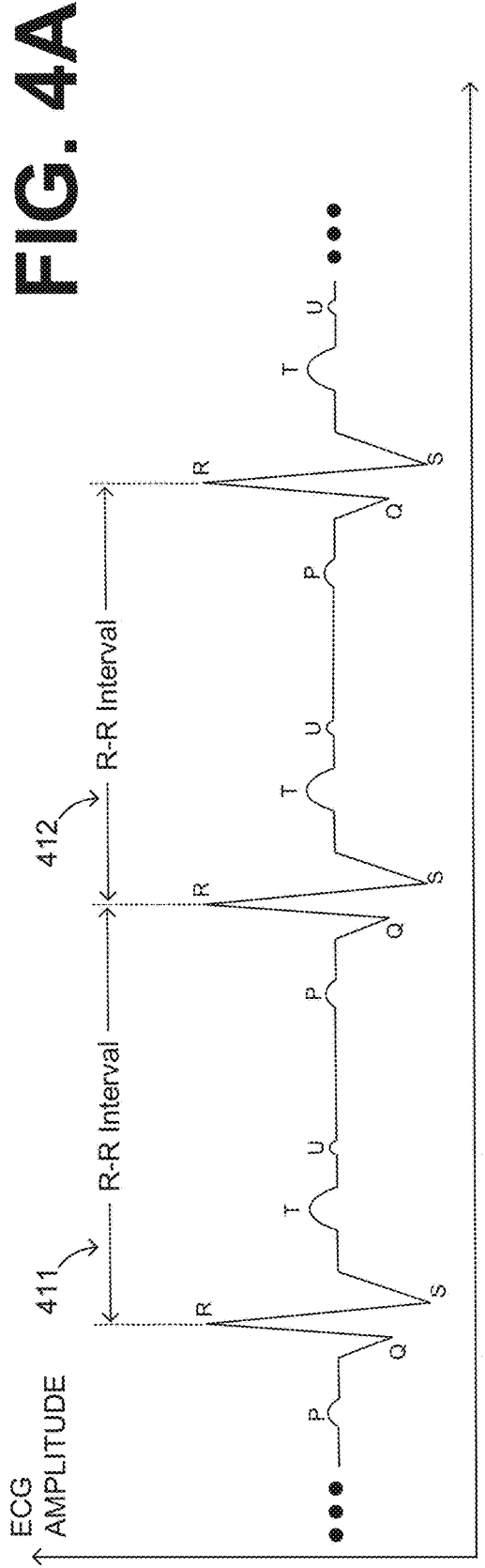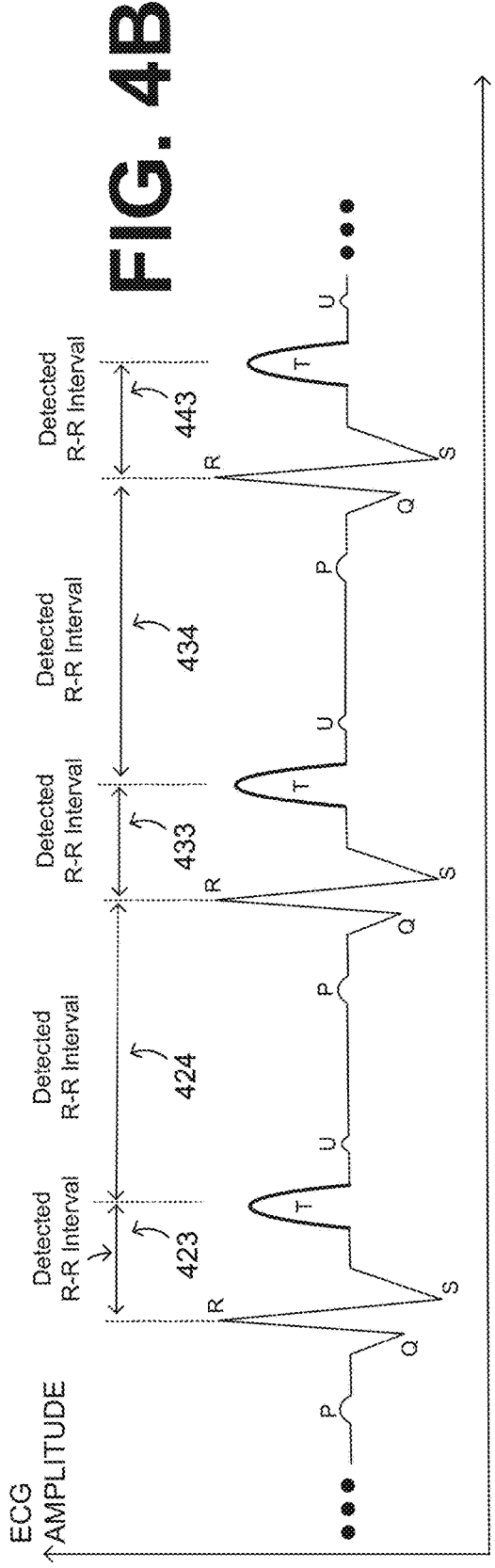

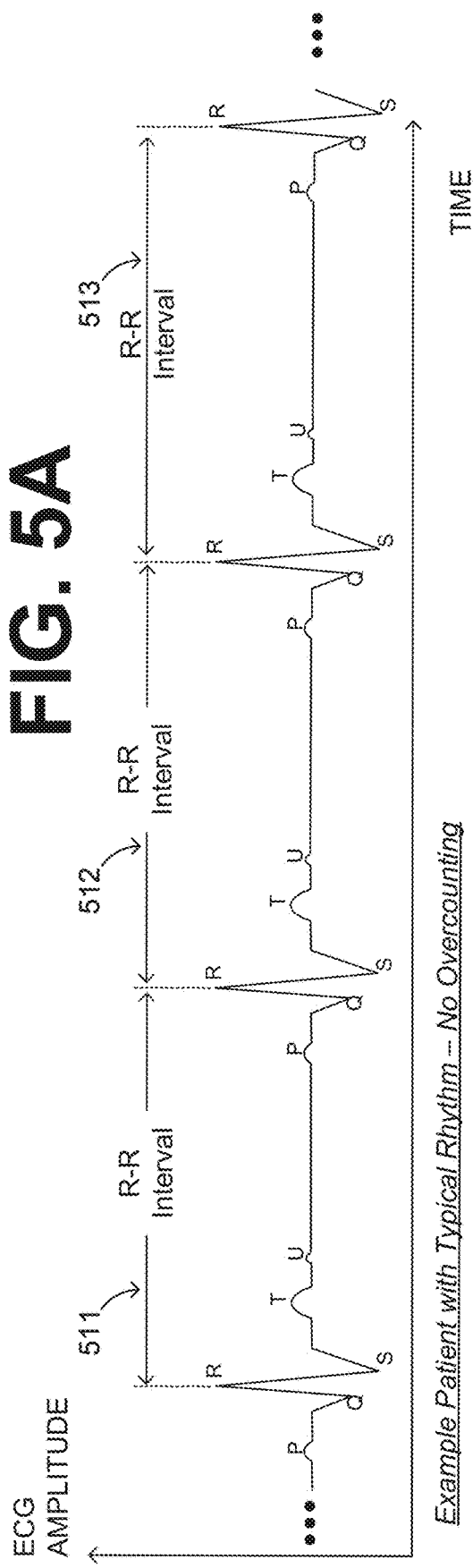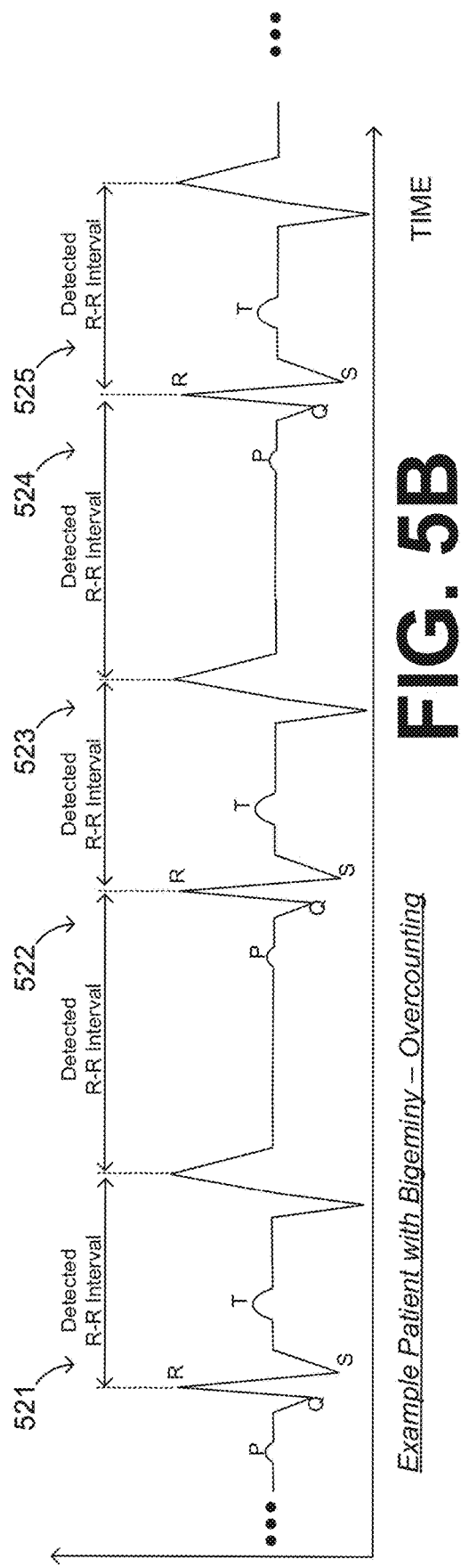

HEART RATE DETERMINATION WITH
REDUCED OVERCOUNTING

HEART RATE CALCULATOR WITH REDUCED OVERCOUNTING

CROSS-REFERENCE TO RELATED APPLICATIONS

This patent application is a divisional application of U.S. patent application Ser. No. 16/140,324, filed on Sep. 24, 2018, entitled HEART RATE CALCULATOR WITH REDUCED OVERCOUNTING, now issued as U.S. Pat. No. 11,364,387 on Jun. 21, 2022, which claims the benefit of U.S. Provisional Patent Application No. 62/538,172, filed on Jul. 28, 2017, the entire disclosures of which are hereby incorporated by reference in their entirety for all purposes.

BACKGROUND

When people suffer from some types of heart arrhythmias, the result may be that blood flow to various parts of the body is reduced. Some arrhythmias may even result in a Sudden Cardiac Arrest (SCA). SCA can lead to death very quickly, e.g. within 10 minutes, unless treated in the interim.

Some people have an increased risk of SCA. People at a higher risk include patients who have had a heart attack, or a prior SCA episode. Some doctors recommend an Implantable Cardioverter Defibrillator (ICD) for these people. The ICD is surgically implanted in a patient and can deliver an electric shock to treat certain arrhythmias.

After being identified as having an increased risk of an SCA, and before receiving an ICD, these people are sometimes given a Wearable Cardioverter Defibrillator (WCD) system. (Early versions of such systems were called wearable cardiac defibrillator systems.) A WCD system typically includes a harness, vest, or other garment that the patient is to wear. The WCD system further includes electronic components, such as a defibrillator and electrodes, coupled to the harness, vest, or other garment. When the patient wears the WCD system, the external electrodes may then make good electrical contact with the patient's skin, and therefore can help sense the patient's ECG. If a shockable heart arrhythmia is detected, then the defibrillator delivers the appropriate electric shock through the patient's body, and thus through the heart.

Often the patient's ECG includes electrical noise, which can be created at the interface of the electrodes with the patient's skin. Such noise can make it difficult to diagnose the patient's condition accurately from the ECG and detect whether or not the patient is having a shockable arrhythmia.

In some cases, a WCD includes a heart rate (HR) monitor function that measures the patient's HR using the patient's ECG. The HR monitor function can provide the HR as an indication of the patient's condition, and in some cases may also be used in determining whether the patient has a shockable rhythm.

All subject matter discussed in this Background section of this document is not necessarily prior art and should not be presumed to be prior art simply because it is presented in this Background section. Plus, any reference to any prior art in this description is not, and should not be taken as, an acknowledgement or any form of suggestion that such prior art forms parts of the common general knowledge in any art in any country. Any recognition of a problem in the prior art discussed in this Background section or associated with such subject matter may be a unique appreciation or recognition of the problem or existence of the problem by the inventor(s) and, thus, should not be treated as prior art unless expressly stated to be prior art. Rather, the discussion of any subject matter in this Background section should be treated as part of the approach taken towards the particular problem by the inventors. This approach in and of itself may also be inventive.

BRIEF SUMMARY

The present description describes various aspects of a HR calculator, some embodiments of which can be used advantageously in WCD systems. Some embodiments can be used in devices other than WCDs. In aspects, embodiments of a HR calculator can include one or more ECG sensors and a processor having a memory configured with: classification criteria to classify a received ECG signal into one of a plurality of ECG rhythm types; for each of the plurality of ECG rhythm types a corresponding algorithm or set of instructions to determine the patient's heart rate. The processor is configured to use the classification criteria to identify the ECG signal's type and determine a heart rate of the patient using the identified type's corresponding algorithm.

In other aspects, embodiments of a HR calculator use a recurring interval of the patient's ECG to determine a HR. The HR monitor is configurable to avoid overcounting of erroneous measurements of the intervals that can result from large T-waves and/or bigeminy by comparing the mean of even intervals with the mean of odd intervals. If the means are significantly different double counting or bigeminy is indicated and the HR calculation is adjusted accordingly.

In another aspect, embodiments of a HR calculator according to the present disclosure measure HR from the patient's ECG by detecting QRS complexes to determine an average R-R interval, which is then used to determine the patient's HR. Further, according to this aspect, the HR calculator is configured to avoid overcounting of QRS complexes and/or erroneous measurements of the R-R intervals that can result from the patient's heart generating "large" T-waves that can be erroneously detected as QRS complexes.

In still another aspect, embodiments of a HR calculator according to the present disclosure also measure HR from the patient's ECG by detecting QRS complexes to determine an average R-R interval, which is then used to determine the patient's HR. Further, according to this aspect, the HR calculator is configured to avoid overcounting of QRS complexes and/or erroneous measurements of the R-R intervals that can result from the patient having a heart rhythm in which every other heart beat is abnormal. This condition is sometimes referred to as bigeminy.

In yet another aspect, embodiments of a HR calculator according to the present disclosure incorporate both aspects described above. That is, the embodiments are configured to detect bigeminy and are also configured to detect double counting of QRS complexes caused by large T-waves.

BRIEF DESCRIPTION OF THE DRAWINGS

FIG. 4A is a diagram illustrating a portion of an ECG analyzed by a HR calculator resulting in no overcounting, according to embodiments.

FIG. 4B is a diagram illustrating a portion of an ECG analyzed by a HR calculator resulting in overcounting due to large T-waves, according to embodiments.

FIG. 5A is a diagram illustrating a portion of an ECG analyzed by a HR calculator resulting in no overcounting, according to embodiments.

FIG. 5B is a diagram illustrating a portion of an ECG analyzed by a HR calculator resulting in overcounting due to bigeminy, according to embodiments

DETAILED DESCRIPTION

The present description discloses several embodiments of a HR calculator with reduced overcounting, which can be used advantageously in WCD systems, media that store instructions, and methods.

A wearable cardioverter defibrillator (WCD) system made according to embodiments has a number of components. These components can be provided separately as modules that can be interconnected, or can be combined with other components, etc.

Figure 1:
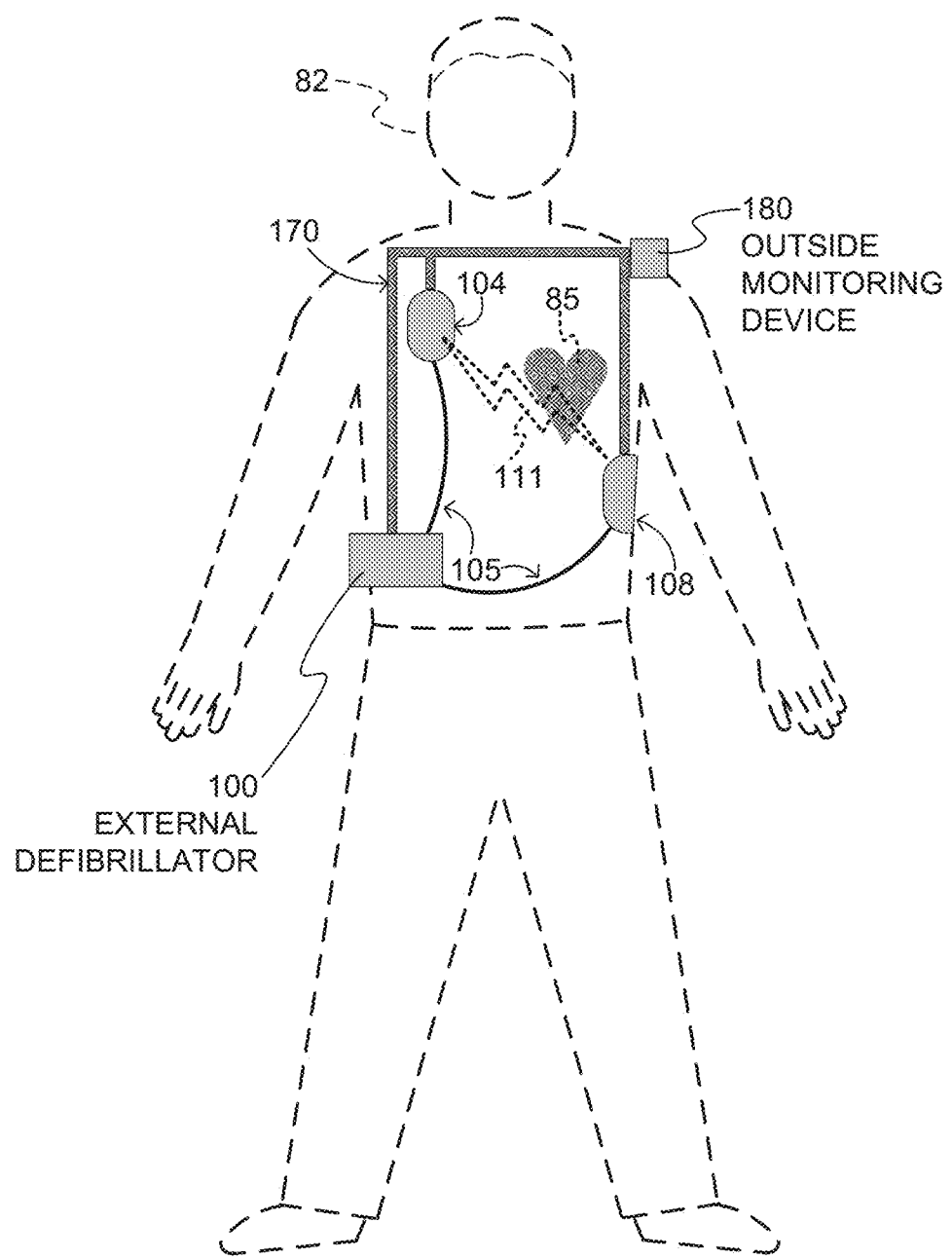
FIG. 1 is a diagram showing components of a WCD system, according to embodiments.

FIG. 1 depicts a patient 82. Patient 82 may also be referred to as a person and/or wearer, since the patient is wearing components of the WCD system. Patient 82 is ambulatory, which means patient 82 can walk around, and is not necessarily bed-ridden.

FIG. 1 also depicts components of a WCD system made according to embodiments. One such component is a support structure 170 that is wearable by patient 82. It will be understood that support structure 170 is shown only generically in FIG. 1, and in fact partly conceptually. FIG. 1 is provided merely to illustrate concepts about support structure 170 and is not to be construed as limiting how support structure 170 is implemented, or how it is worn.

Support structure 170 can be implemented in many different ways, in accordance with various embodiments of the present disclosure. For example, in some embodiments, support structure 170 can be implemented in a single component or a combination of multiple components. In embodiments, support structure 170 could include a vest, a half-vest, a garment, etc. In such embodiments such items can be worn similarly to parallel articles of clothing. In embodiments, support structure 170 could include a harness, one or more belts or straps, etc. In such embodiments, such items can be worn by the patient around the torso, hips, over the shoulder, etc. In embodiments, support structure 170 can include a container or housing, which can even be waterproof. In such embodiments, the support structure can be worn by being attached to the patient by adhesive material, for example as shown in U.S. Pat. No. 8,024,037. Support structure 170 can even be implemented as described for the support structure of US Pat. App. No. US2017/0056682, which is incorporated herein by reference. Of course, in such embodiments, the person skilled in the art will recognize that additional components of the WCD system can be in the housing of a support structure instead of being attached externally to the support structure, for example as described in the US2017/0056682 document. There can be other examples.

A WCD system according to embodiments is configured to defibrillate a patient who is wearing it, by delivering an electrical charge to the patient's body in the form of an electric shock delivered in one or more pulses. FIG. 1 shows an illustrative external defibrillator 100 and defibrillation electrodes 104, 108, which are coupled to external defibrillator 100 via electrode leads 105. Defibrillator 100 and defibrillation electrodes 104, 108 can be coupled to support structure 170. As such, many of the components of defibrillator 100 could be therefore coupled to support structure 170. When defibrillation electrodes 104, 108 are in electrical contact with the body of patient 82, defibrillator 100 can administer, via electrodes 104, 108, a brief, strong electric pulse 111 through the body. Pulse 111 is also known as shock, defibrillation shock, therapy and therapy shock. Pulse 111 is intended to go through and restart heart 85, in an effort to save the life of patient 82. Pulse 111 can further include one or more pacing pulses, and so on.

Embodiments of external defibrillator 100 are configured to decide whether to defibrillate or not based at least in part on an analysis of an ECG signal of the patient. In some embodiments, external defibrillator 100 in configured to initiate defibrillation (or hold-off defibrillation) based on a variety of inputs, with ECG being one of them.

After review of the present disclosure, a person skilled in the art will appreciate that several signals, such as physiological signals containing physiological data, can be obtained from patient 82. While the patient may be considered also a "user" of the WCD system, this is not a requirement in some embodiments. That is, for example, a user of the WCD may include a clinician such as a doctor, nurse, emergency medical technician (EMT) or other similarly situated individual (or group of individuals). The particular context of these and other related terms within this description should be interpreted accordingly.

Further, in embodiments external defibrillator 100 also includes a heart rate (HR) calculator (not shown) configured to determine the heart rate of patient 82 from the patient's ECG. Embodiments of the HR calculator described below in conjunction with FIGS. 3-8 are configured to determine the HR with reduced overcounting.

Some embodiments of the WCD system include an outside monitoring device 180. Device 180 is referred to herein as an "outside" device because it could be provided as a standalone device, for example not within the housing of defibrillator 100. Embodiments of device 180 can be configured to sense or monitor at least one local parameter. A local parameter can be a parameter of patient 82, or a parameter of the WCD system, or a parameter of the environment, as will be described later in this document. In embodiments, device 180 may include one or more transducers or sensors that are configured to render one or more physiological inputs or signals from one or more patient parameters that they sense.

In some embodiments, device 180 is physically coupled to support structure 170. In addition, device 180 can be communicatively coupled with other components, which are coupled to support structure 170. Such communication can be implemented by a communication module, as deemed applicable in view of this description by a person skilled in the art.

Figure 2:
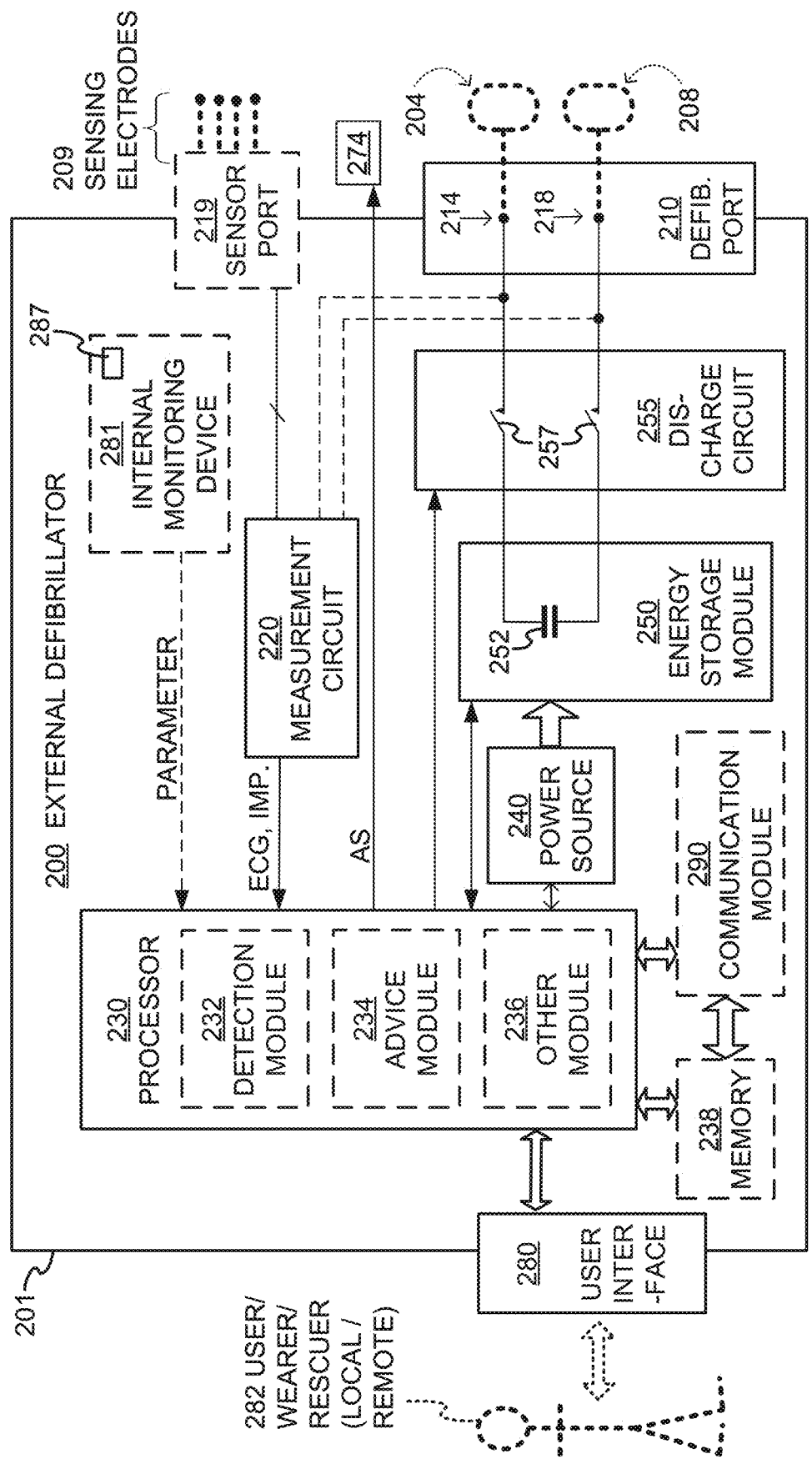
FIG. 2 is a diagram showing components of an external defibrillator, such as depicted in the system of FIG. 1, according to embodiments.

FIG. 2 is a diagram showing components of an external defibrillator 200, according to embodiments. These components can be, for example, included in external defibrillator 100 of FIG. 1. The components shown in FIG. 2 can be provided in a housing 201, which may also be referred to as casing 201.

According to embodiments, external defibrillator 200 is configured for or adapted to a patient who would be wearing it, such as patient 82 of FIG. 1. Embodiments of defibrillator 200 may further include a user interface 280 for a user 282. User 282 can be patient 82, also known as wearer 82. Or, user 282 can be a local rescuer at the scene, such as a bystander who might offer assistance, or a trained person. Or, user 282 might be a remotely located trained caregiver in communication with the WCD system.

In various embodiments, user interface 280 includes output devices that are visual, audible and/or tactile, for communicating to a user by outputting images, sounds and/or vibrations. Images, sounds, vibrations, and anything that can be perceived by user 282 are also human-perceptible indications according to embodiments. There are many other output devices that can be used in various embodiments. For example, in various embodiments the output device can be a light source, or a screen to display what is sensed, detected and/or measured, and provide visual feedback to rescuer 282 for their resuscitation attempts, and so on. Another output device can be a speaker, which can be configured to issue voice prompts, beeps, alarm sounds and/or words to warn bystanders, etc.

In embodiments, user interface 280 includes input devices for receiving inputs from users. In some embodiments, such input devices include various controls, such as pushbuttons, keyboards, touchscreens, one or more microphones, and so on. An input device can be a cancel switch, which is sometimes called an "I am alive" switch or "live man" switch. In some embodiments, actuating the cancel switch can prevent the impending delivery of a shock.

Defibrillator 200 includes an internal monitoring device 281 in some embodiments. Device 281 is referred to herein as an "internal" device because it is incorporated within housing 201. In various embodiments, monitoring device 281 can sense or monitor patient parameters such as patient physiological parameters, system parameters and/or environmental parameters, all of which can be called patient data. In other words, internal monitoring device 281 can be complementary or an alternative to outside monitoring device 180 of FIG. 1. Allocating which of the parameters are to be monitored by which of monitoring devices 180, 281 in various embodiments depending on the application. In embodiments, device 281 may include one or more transducers or sensors that are configured to render one or more physiological inputs from one or more patient parameters that it senses.

As used herein, patient parameters include patient physiological parameters. Patient physiological parameters may include, for example and without limitation, those physiological parameters that can be of any help in detecting by the wearable defibrillation system whether the patient is in need of a shock. In some embodiments, patient parameters include the patient's medical history and/or event history. Examples of such parameters include the patient's ECG, blood oxygen level, blood flow, blood pressure, blood perfusion, pulsatile change in light transmission or reflection properties of perfused tissue, heart sounds, heart wall motion, breathing sounds and pulse. Accordingly, monitoring devices 180, 281 may include one or more sensors configured to acquire patient physiological signals. Examples of such sensors or transducers include electrodes to detect ECG data, a perfusion sensor, a pulse oximeter, a device for detecting blood flow (e.g. a Doppler device), a sensor for detecting blood pressure (e.g. a cuff), an optical sensor, illumination detectors and sensors perhaps working together with light sources for detecting color change in tissue, a motion sensor, a device that can detect heart wall movement, a sound sensor, a device with a microphone, an $SpO_2$ sensor, and so on. In view of this disclosure, it will be appreciated that such sensors can help detect the patient's pulse, and can therefore also be called pulse detection sensors, pulse sensors, and pulse rate sensors. Pulse detection is also taught at least in Physio-Control's U.S. Pat. No. 8,135,462, which is hereby incorporated by reference in its entirety. In addition, a person skilled in the art may implement other ways of performing pulse detection. In such cases, the transducer includes an appropriate sensor, and the physiological input is a measurement by the sensor of that patient parameter. For example, in some embodiments the appropriate sensor for a heart sound includes a microphone, transducer, etc.

In some embodiments, the local parameter is a trend that can be detected in a monitored physiological parameter of patient 282. A trend can be detected by comparing values of parameters at various times. Parameters whose detected trends can particularly help a cardiac rehabilitation program include: a) cardiac function (e.g. ejection fraction, stroke volume, cardiac output, etc.); b) heart rate variability at rest or during exercise; c) heart rate profile during exercise and measurement of activity vigor, such as from the profile of an accelerometer signal and informed from adaptive rate pacemaker technology; d) heart rate trending; e) perfusion, such as from $SpO_2$ or $CO_2$; f) respiratory function, respiratory rate, etc.; g) motion, level of activity; and so on. Once a trend is detected, it can be stored and/or reported via a communication link, along perhaps with a warning. From the report, a physician monitoring the progress of patient 282 will know about a condition that is either not improving or deteriorating.

Patient state parameters include recorded aspects of patient 282, such as motion, posture, whether they have spoken recently, what they said, and so on, and optionally the history of these parameters. One of these monitoring devices could include a location sensor such as a Global Positioning System (GPS) location sensor. Such a sensor can detect the location, plus a speed can be detected as a rate of change of location over time. Many motion detectors output a motion signal that is indicative of the motion of the detector, and thus of the patient's body. Patient state parameters can be very helpful in narrowing down the determination of whether SCA is indeed taking place.

A WCD system made according to embodiments may include a motion detector. In embodiments, a motion detector can be implemented within monitoring device 180 or monitoring device 281. Such a motion detector can be made in many ways as is known in the art, for example by using an accelerometer. In this example, a motion detector 287 is implemented within monitoring device 281.

A motion detector of a WCD system according to embodiments can be configured to detect a motion event. In response, the motion detector may render or generate, from the detected motion event or motion, a motion detection input that can be received by a subsequent device or functionality. A motion event can be defined as is convenient, for example a change in motion from a baseline motion or rest, etc. In such cases, a sensed patient parameter is motion.

System parameters of a WCD system can include system identification, battery status, system date and time, reports of self-testing, records of data entered, records of episodes and intervention, and so on.

Environmental parameters can include ambient temperature and pressure. Moreover, a humidity sensor may provide information as to whether it is likely raining. Presumed patient location could also be considered an environmental parameter. The patient location could be presumed, if monitoring device 180 or 281 includes a GPS location sensor as per the above, and if it is presumed that the patient is wearing the WCD system.

Defibrillator 200 typically includes a defibrillation port 210, such as a socket in housing 201. Defibrillation port 210 includes electrical nodes 214, 218. Leads of defibrillation electrodes 204, 208, such as leads 105 of FIG. 1, can be plugged into defibrillation port 210, so as to make electrical contact with nodes 214, 218, respectively. It is also possible that defibrillation electrodes 204, 208 are connected continuously to defibrillation port 210, instead. Either way, defibrillation port 210 can be used for guiding, via electrodes, to the wearer the electrical charge that has been stored in an energy storage module 250 that is described more fully later in this document. The electric charge will be the shock for defibrillation, pacing, and so on.

In some embodiments, defibrillator 200 also has a sensor port 219 in housing 201, which is also sometimes known as an ECG port. In some embodiments, sensor port 219 is adapted to enable the plugging in of sensing electrodes 209, which are also known as ECG electrodes and ECG leads. In some embodiments sensing electrodes 209 can be connected continuously to sensor port 219, instead. Sensing electrodes 209 are types of transducers that can help sense an ECG signal, e.g. a 12-lead signal, or a signal from a different number of leads, especially if they make good electrical contact with the body of the patient and in particular with the skin of the patient. Sensing electrodes 209 can be attached to the inside of support structure 170 for making good electrical contact with the patient, similarly with defibrillation electrodes 204, 208.

Optionally a WCD system according to embodiments also includes a fluid that it can deploy automatically between the electrodes and the patient's skin. The fluid can be conductive, such as by including an electrolyte, for establishing a better electrical contact between the electrode and the skin. Electrically speaking, when the fluid is deployed, the electrical impedance between the electrode and the skin is reduced. Mechanically speaking, the fluid may be in the form of a low-viscosity gel, so that it does not flow away from the electrode, after it has been deployed. The fluid can be used for both defibrillation electrodes 204, 208, and for sensing electrodes 209.

The fluid may be initially stored in a fluid reservoir, not shown in FIG. 2, which can be coupled to the support structure. In addition, a WCD system according to embodiments further includes a fluid deploying mechanism 274. Fluid deploying mechanism 274 is some embodiments is configured to cause at least some of the fluid to be released from the reservoir and be deployed near one or both of the patient locations, to which the electrodes are configured to be attached to the patient. In some embodiments, fluid deploying mechanism 274 is activated prior to the electrical discharge responsive to receiving activation signal AS from a processor 230, which is described more fully later in this document.

Embodiments of defibrillator 200 also include a measurement circuit 220, as one or more of its sensors or transducers. Measurement circuit 220 senses one or more electrical physiological signals of the patient from sensor port 219, in embodiments where they are provided. Even in embodiments in which defibrillator 200 lacks sensor port 219, some embodiments of measurement circuit 220 obtain physiological signals through nodes 214, 218 instead, when defibrillation electrodes 204, 208 are attached to the patient. In these cases, the physiological input reflects or is derived from an ECG measurement. In some embodiments a patient parameter is an ECG, which is sensed as a voltage difference between electrodes 204, 208. In addition, in some embodiments a patient parameter is an impedance, which can be sensed between electrodes 204, 208 and/or the connections of sensor port 219. Sensing the impedance can be useful for detecting, among other things, whether these electrodes 204, 208 and/or sensing electrodes 209 are not making good electrical contact with the patient's body. These patient physiological signals are sensed in some embodiments. Embodiments of measurement circuit 220 are configured to render or generate information about them as physiological inputs, data, other signals, etc. That is, the information rendered by measurement circuit 220 is output from it, but this information can be called an input because this information is received by a subsequent device or functionality as an input.

Defibrillator 200 also includes a processor 230. Processor 230 may be implemented in a number of ways in various embodiments. Such ways include, by way of example and not of limitation, digital and/or analog processors such as microprocessors and Digital Signal Processors (DSPs); controllers such as microcontrollers; software running in a machine; programmable circuits such as Field Programmable Gate Arrays (FPGAs), Field-Programmable Analog Arrays (FPAAs), Programmable Logic Devices (PLDs), Application Specific Integrated Circuits (ASICs), any combination of one or more of these, and so on.

Processor 230 may include, or have access to, a non-transitory storage medium, such as memory 238 that is described more fully later in this document. Such a memory can have a non-volatile component for storage of machine-readable and machine-executable instructions. A set of such instructions can also be called a program. The instructions, which may also be referred to as "software," generally provide functionality by performing methods as may be disclosed herein or understood by one skilled in the art in view of the disclosed embodiments. In some embodiments, and as a matter of convention used herein, instances of the software may be referred to as a "module" and by other similar terms. Generally, a module includes a set of the instructions so as to offer or fulfill a particular functionality. Embodiments of modules and the functionality delivered are not limited by the embodiments described in this document. Processor 230 may, among other functions, set a flag, unset a flag, and so on. In some embodiments, processor 230 includes a multi-core processor in which a particular core or cores are configured or "dedicated" to perform certain functions and/or implement selected modules, while other core or cores are configured to perform other functions and/or selected modules.

In various embodiments, processor 230 is configured to have a number of modules. In some embodiments, one such module is a detection module 232. Detection module 232 includes a Ventricular Fibrillation (VF) detector in some embodiments. In such embodiments, the patient's sensed ECG from measurement circuit 220, which is available as physiological inputs, data, or other signals, is used by the VF detector to determine whether the patient is experiencing VF. Detecting VF is useful, because VF typically results in SCA. In some embodiments, detection module 232 also includes a Ventricular Tachycardia (VT) detector, and so on.

In some embodiments, another such module in processor 230 is an advice module 234, which generates advice for what the system is to do. The advice can be based on outputs of detection module 232. There can be many types of advice according to various embodiments. In some embodiments, the advice is a shock/no shock determination that processor 230 makes, for example via advice module 234. The shock/no shock determination is made by executing a stored Shock Advisory Algorithm in some embodiments. A Shock Advisory Algorithm makes a shock/no shock determination from one or more ECG signals that are captured according to embodiments and determining whether a shock criterion is met. The determination is made from a rhythm analysis of the captured ECG signal in some embodiments. In other embodiments, other physiological and/or environmental inputs are used by the Shock Advisory Algorithm in addition to or instead of the ECG signal.

In some embodiments, when the determination is to shock, an electrical charge is delivered to the patient. Delivering the electrical charge is also known as discharging. Shocking can be for defibrillation, pacing, and so on.

In some embodiments, processor 230 includes additional modules, such as other module 236, for other functions. In addition, in embodiments having internal monitoring device 281, internal monitoring device 281 may be operated in part by processor 230, etc.

In some embodiments, defibrillator 200 further includes a memory 238, which is configured to work together with processor 230. Memory 238 is implemented in a number of ways according to various embodiments. Such ways include, by way of example and not of limitation, volatile memories, Nonvolatile Memories (NVM), Read-Only Memories (ROM), Random Access Memories (RAM), magnetic disk storage media, optical storage media, smart cards, flash memory devices, any combination of these, and so on. Memory 238 is thus a non-transitory storage medium. In some embodiments that include memory 238, the memory includes programs for processor 230, which processor 230 is configured to read and execute. The programs can include sets of instructions in the form of code, which processor 230 is able to read and execute. Executing is performed by physical manipulations of physical quantities, and depending on the program, results in functions, operations, processes, actions and/or methods to be performed, and/or the processor to cause other devices or components or blocks to perform such functions, operations, processes, actions and/or methods. The programs can be operational for the inherent needs of processor 230 and can also include protocols and ways that decisions can be made by advice module 234. In addition, memory 238 is configurable to store prompts for user 282, if this user is a local rescuer. Moreover, memory 238 is used in some embodiments to store data. This data can include patient data, system data and environmental data, for example as learned by internal monitoring device 281 and outside monitoring device 180. The data can be stored in memory 238 before it is transmitted out of defibrillator 200 or stored there after it is received by defibrillator 200.

Defibrillator 200 also includes a power source 240, according to some embodiments of the present invention. To enable portability of defibrillator 200, power source 240 includes a battery in some embodiments. In some embodiments the battery is implemented as a rechargeable battery pack, while in other embodiments the battery pack is not rechargeable. Some embodiments use a combination of rechargeable and non-rechargeable battery packs. Other embodiments of power source 240 include an AC power override, for where AC power will be available, and/or an energy-storing capacitor, and so on. In some embodiments, power source 240 is controlled by processor 230. Appropriate components (not shown) are included to provide for charging or replacing power source 240.

Defibrillator 200 may additionally include an energy storage module 250. Energy storage module 250 can be coupled to the support structure of the WCD system, for example either directly or via the electrodes and their leads. Module 250 is where some electrical energy can be stored temporarily in the form of an electrical charge, when preparing it for discharge to administer a shock. In embodiments, module 250 can be charged from power source 240 to the desired amount of energy, as controlled by processor 230. In typical implementations, module 250 includes a capacitor 252, which can be a single capacitor or a system of capacitors, and so on. In some embodiments, energy storage module 250 includes a device that exhibits high power density, such as an ultracapacitor. As described above, capacitor 252 can store the energy in the form of an electrical charge, for delivering to the patient.

Defibrillator 200 moreover includes a discharge circuit 255. When the decision is to shock, processor 230 can be configured to control discharge circuit 255 to discharge through the patient the electrical charge stored in energy storage module 250. When so controlled, circuit 255 can permit the energy stored in module 250 to be discharged to nodes 214, 218, and from there also to defibrillation electrodes 204, 208, so as to cause a shock to be delivered to the patient. Circuit 255 can include one or more switches 257. Switches 257 can be made in a number of ways, such as by an H-bridge, and so on. Circuit 255 can also be controlled via user interface 280.

Defibrillator 200 can optionally include a communication module 290, for establishing one or more wired or wireless communication links with other devices of other entities, such as a remote assistance center, Emergency Medical Services (EMS), and so on. The data can include patient data, event information, therapy attempted, CPR performance, system data, environmental data, and so on. For example, communication module 290 may transmit wirelessly, e.g. on a daily basis, heart rate, respiratory rate, and other vital signs data to a server accessible over the internet, for instance as described in US 20140043149. This data can be analyzed directly by the patient's physician and can also be analyzed automatically by algorithms designed to detect a developing illness and then notify medical personnel via text, email, phone, etc. Module 290 may also include such interconnected sub-components as may be deemed necessary by a person skilled in the art, for example an antenna, portions of a processor, supporting electronics, outlet for a telephone or a network cable, etc. This way, data, commands, etc. can be communicated.

Defibrillator 200 can optionally include other components.

Figure 3:
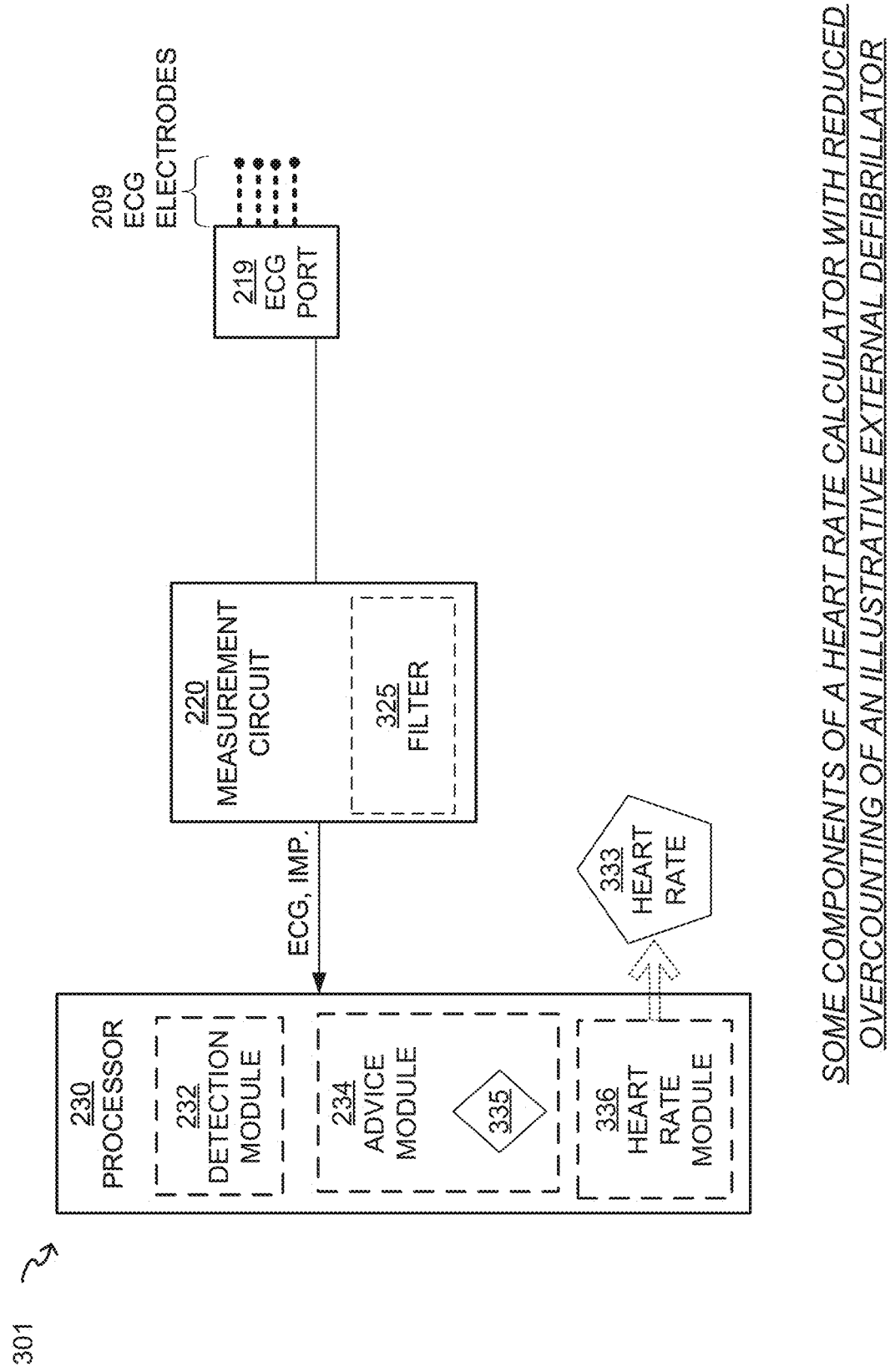
FIG. 3 is a diagram illustrating a partial view of the components of an external defibrillator with a HR calculator with reduced overcounting, according to embodiments.

FIG. 3 is a diagram illustrating in more detail some of the components 301 of external defibrillator 200 (FIG. 2) that are used in implementing a HR calculator with reduced overcounting, according to embodiments. Further, in some embodiments the HR calculator is configured to provide other information related to the patient's heart rhythm, as will be described below. Still further, the HR calculator can be implemented in devices other than a WCD. For example, the HR calculator can be implemented in a monitor defibrillator, an AED, a vital signs monitor, a fitness tracker, or other device that monitors a patient's HR.

In embodiments, measurement circuit 220 includes a filter 325 to attenuate at least some of the noise that may be present on the ECG signal received from ECG port 219 and ECG electrodes 209. In various embodiments, filter 325 is implemented as an analog filter, a digital filter, or combinations of both. In some embodiments, filter 325 is implemented in whole or in part in processor 230 rather than solely in measurement circuit 220. In some embodiments, defibrillator 200 does not include filter 325.

In embodiments, processor 230 includes modules 232 and 234 as described in conjunction with FIG. 2, and in addition includes a HR module 336 configured to calculate and output a HR 333 that is determined from the ECG signal received from measurement circuit 220. Computed heart rate 333 can be used in additional ways in various embodiments. For example, in various embodiments the HR may be stored in memory 238 (FIG. 2), downloaded later from memory 238, transmitted wirelessly via communication module 290 (FIG. 2), displayed by a screen of user interface 280 (FIG. 2), and so on.

In some embodiments, HR module 336 includes a HR calculator that avoids overcounting of R-R intervals that can lead to erroneous measurements of the R-R Intervals of the received ECG signal. For example, hearts rhythms such as bigeminy or rhythms with large T-waves can lead to overcounting of R-R intervals. In embodiments, the R-R interval measurements are used in calculating the HR 333 by determining the equivalent of the inverse(s) of one or more averages of the measured R-R intervals. In some embodiments HR module 336 is configured with: classification criteria to classify a received ECG signal into one of a plurality of ECG rhythm types (e.g., a T-wave double counting type, a bigeminy type, and a default type for all other types of rhythms). Further, for each of the plurality of ECG rhythm types, embodiments of HR module 336 are configured with a corresponding algorithm or set of instructions to determine the patient's heart rate. Embodiments of HR module 336 are configured to use the classification criteria to identify the ECG signal's type and determine a heart rate of the patient using the identified type's corresponding algorithm. In some embodiments, the classification is implemented using a rules-based system. Described below are embodiments of HR module 336 with particular criteria, algorithms etc. for identifying ECG rhythm types and calculating the HR according to the identified ECG rhythm type. For example, in embodiments, the HR module determines an average of the "even" Detected R-R intervals (also referred to herein as the EVEN MEAN) and an average of the "odd" Detected R-R intervals (also referred to herein as the ODD MEAN). As described in more detail below in conjunction with FIG. 4A, an "average" as used in this context can be a mean, median, etc. The average of the "even" intervals and the average of the "odd" intervals can be analyzed to detect potential overcounting as will be described below in conjunction with FIGS. 4A-5B.

FIG. 4A is a diagram schematically illustrating a portion of an ECG analyzed by a HR calculator resulting in no overcounting, according to embodiments. This example ECG portion has "normal" QRS complexes and a "normal" T-wave. As a result, the R-R intervals 411 and 412 are measured based on the detected peaks of each QRS complex (i.e., peaks of the R-waves). In some embodiments, the mean of the R-R intervals over a 4.8 second segment is used to calculate the HR for that segment, with the HR for that time segment being an inverse of the average R-R interval. As used herein in this context, "average" can be a mean, median, mode, a "trimmed mean" that eliminates outliers, or other measure that identifies the central tendency of the R-R interval. For example, in some embodiments when the R-R interval is measured in seconds, the inverse can be 60/median R-R interval to output a HR in beats per minute. In other embodiments, the HR is calculated as an inverse of a running average of the R-R intervals over the most recent 10 seconds. In some embodiments the patient's "instantaneous" HR is calculated as an inverse of the mean of the most recent N R-R intervals, where N ranges from 5 to 20.

FIG. 4B is a diagram schematically illustrating a portion of an ECG analyzed by a HR calculator resulting in overcounting due to large T-waves, according to embodiments. As can be seen in this example ECG, the T-wave peaks are similar in height to the peaks of QRS complexes. When T waves have similar peaks as QRS complexes, it is difficult for conventional ECG-based HR monitors to detect the QRS complexes and avoid these "tall" T waves. In the example of FIG. 4B, a conventional HR monitor would count each T wave as a QRS complex, resulting in double counting of R-R intervals. So, the first "true" R-R interval is erroneously measured as two Detected R-R intervals 423 and 424 in this example ECG portion. Similarly, the next "true" R-R interval in this example is erroneously measured as two Detected R-R intervals 433 and 434, and so on. If both the QRS complexes and the T waves are counted, the situation is particularly problematic because this could lead to an erroneously high heart rate. In a WCD this could lead to an unnecessary shock.

Referring to FIGS. 3 and 4B, some embodiments of HR module 336 implement one or more algorithms that determine: (a) an average of the "odd" intervals (e.g., Detected R-R intervals 423, 433, 443, etc.); (b) an average of the "even" intervals (e.g., Detected R-R intervals 424, 434, etc.); (c) a margin $M_E$ for the "even" intervals; and (d) a margin $M_O$ for the "odd" intervals. In some embodiments, margin $M_E$ and $M_O$ are the same, but can be unequal in other embodiments. Because the QRS detection may begin with a T-wave rather than the R-wave in this large T-wave scenario, the "odd" intervals may begin with a T-wave rather than an R-wave. In some embodiments, the averages of the "odd" and "even" intervals are the medians of these intervals because medians tend to be insensitive to outliers. This can be helpful in some embodiments because if a beat is missed or a beat is double-counted, the heart rate is not significantly affected. On the other hand, if the patient has bigeminy the median tends to pick up on one of the two intervals when the real heart rate is the average of the two intervals. One of the advantages of "median" embodiments is that it allows the use the median R-R interval for normal rhythms (i.e., for most patients) for reduced sensitivity to outliers, but can still detect bigeminy and return a correct heart rate.

In embodiments, the algorithm uses the margins $M_E$ and $M_O$ in determining whether the ODD MEAN and EVEN MEAN are different enough to indicate double counting. In contrast, in a "normal" heart rhythm, the means of the "odd" and "even" intervals are likely to be substantially equal. Further, while it is possible that VF could cause the patient's ECG to occasionally have portions that appear as a large T-wave rhythm, it is very unlikely that the EVEN MEAN will differ from the ODD MEAN by more than sum of the margins $M_E$ and $M_O$.

In some embodiments, the values for $M_E$ and $M_O$ are a scaled version of the standard deviation (a) of "even" intervals and the a of the "odd" intervals, respectively. In embodiments, standard deviations of the "even" and "odd" intervals are calculated from the Detected R-R intervals used to calculate the mean of the "even" and "odd" intervals. In some embodiments, the margin $M_E$ is equivalent to three standard deviations (3σ) of the "even" intervals, and $M_O$ is equivalent to 3σ of the "odd" intervals. In other embodiments, the margins may be determined using other methods such as, for example, a different scaling factor of the standard deviations, a percentage of the mean of the Detected R-R intervals, measures of dispersion the Detected R-R intervals such as the variance, the inter-quartile range (and some combination thereof), or preselected values determined from statistical analysis, including values determined using artificial intelligence techniques.

In some embodiments, HR module 336 implements a threshold (TH) used as part of the determination of whether a difference in the EVEN MEAN and the ODD MEAN is due to T-wave double counting. Stated another way, HR module 336 is configured to find whether a Detected R-R interval is actually an R-T interval. As previously mentioned, because the QRS detection may "begin" with a T-wave rather than the R-wave in this scenario, HR module 336 is configured to test both the "even" and "odd" intervals as being R-T intervals. To address these scenarios, in some embodiments HR module 336 is configured with criteria or rules or sets of instructions to determine whether the "even" and "odd" intervals are substantially different. For example, some embodiments of HR module 336 are configured to compare the EVEN MEAN to the ODD MEAN and to detect that a potential T-wave double counting rhythm exists if both Equation (1) and Equation (2) are satisfied, or if both Equation (3) and Equation (4) are satisfied:

$$(\text{EVEN MEAN} + M_E) < (\text{ODD MEAN} - M_O) \quad (1)$$

and $$(\text{EVEN MEAN}) < \text{TH} \quad (2)$$

or $$(\text{ODD MEAN} + M_O) < (\text{EVEN MEAN} - M_E) \quad (3)$$

and $$(\text{ODD MEAN}) < \text{TH} \quad (4)$$

In some embodiments, the value of TH is set as a function of the refractory period that is a parameter of the QRS detection algorithm. In embodiments, the refractory period starts at the detection point on the QRS complex (usually near the peak) and lasts for a fixed duration of time. In some embodiments, the refractory period is 110 ms, but can range from 75 to 300 ms in other embodiments. As used herein in this context, the refractory period does not refer to the vulnerable period, which is based on action potentials in the patient's heart muscle. In some embodiments, the value of TH is set to about twice the refractory period or 240 ms, but in other embodiments the value of TH can range from 100 to 300 ms. Because T-waves typically occur within the refractory period in a normal rhythm, equations (2) and (4) can serve to confirm that EVEN MEAN or ODD MEAN corresponds to an average duration of the R-T intervals and, therefore, T-wave overcounting has been detected. As described earlier, T-wave overcounting can lead to an erroneous HR determination if a conventional HR algorithm is used.

In response to HR module 336 detecting T-wave double counting, some embodiments of HR module 336 are configured to output an indication or alert that T-wave overcounting has been detected. This notification can be received by other modules of processor 230 and provided to the patient via interface 280, stored in memory 238, and/or communicated to other devices via communication module 290. In addition, some embodiments of HR module 336 are further configured to determine the EVEN MEAN and ODD MEAN in seconds and to output HR 333 in beats per minute according to equation (5).

$$\text{HR} = 60/(\text{EVEN MEAN} + \text{ODD MEAN}) \quad (5)$$

In some embodiments, HR 333 is substantially equal to the HR determined according to Equation (5) with rounding to the nearest integer or other selected accuracy.

On the other hand, if T-wave double counting is not detected, embodiments of HR module 336 are configured to treat both "even" and "odd" intervals as normal R-R intervals as described above in conjunction with FIG. 4A. In some embodiments, HR module 366 will output HR 333 by determining the inverse of the mean of all the intervals used to determine EVEN MEAN and ODD MEAN. In some embodiments, HR 333 is substantially equal to the HR according inverse of the mean of all such intervals with rounding to the nearest integer or other selected accuracy.

FIG. 5A is a diagram schematically illustrating a portion of an ECG analyzed by a HR calculator resulting in no overcounting. FIG. 5A is substantially similar to the ECG portion depicted in FIG. 4A and reproduced for easier comparison to a bigeminy ECG portion schematically shown in FIG. 5B.

This example bigeminy ECG portion shows QRS complexes that are each followed by waves from an abnormal contraction that occurs relatively quickly after the QRS complex and before the next "normal" QPR complex. Conventional ECG-based HR monitors can detect the abnormal contraction as a normal heartbeat, which will cause the HR monitor to output a HR that is too high if the segment includes one more abnormal heartbeat than normal heartbeat. In the example of FIG. 5B, a conventional HR monitor would count as a "normal" R-R interval each of intervals 521, 522, 523, 524 and so on. Typically, the HR for a bigeminy rhythm is determined using the mean of the intervals of complete pairs of normal and premature heartbeats. To illustrate a potential problem with conventional HR monitors in analyzing bigeminy rhythms, if for example the segment being analyzed started just before interval 521 and ended just after interval 524, the segment would include an "unpaired" heartbeat with corresponding interval 521. Thus, a conventional HR monitor would take the mean of three "short" intervals (521, 523, 525) and two "long" intervals (522 and 524), which would result in an inaccurate (i.e., smaller) mean of the R-R intervals. This would cause the conventional HR monitor to output an erroneously high heart rate, which if used by a WCD could lead to an unnecessary shock.

Referring to FIGS. 3 and 5B, some embodiments of HR module 336 implement one or more algorithms that determine: (a) the mean of the "odd" intervals (e.g., Detected R-R intervals 521, 523, 525, etc.); (b) the mean of the "even" intervals (e.g., Detected R-R intervals 522, 524, etc.); (c) a margin $M_E$ for the "even" intervals; and (d) a margin $M_O$ for the "odd" intervals. Because the QRS detection may begin with the premature contraction rather than the R-wave in this bigeminy scenario, in such cases the "odd" intervals may be the "long" intervals, as opposed to the "short" intervals as shown in FIG. 5B when the segment begins with the R-wave of a normal QRS complex.

In embodiments, the algorithm uses the margins $M_E$ and $M_O$ in determining whether the ODD MEAN and EVEN MEAN are different enough to indicate bigeminy. In some embodiments, the values for $M_E$ and $M_O$ are a scaled version of the standard deviation (σ) of "even" intervals and the a of the "odd" intervals, respectively. In embodiments, standard deviations of the "even" and "odd" intervals are calculated from the Detected R-R intervals used to calculate the mean of the "even" and "odd" intervals. In some embodiments, similar to embodiments for detecting T-wave overcounting, the margin $M_E$ is equivalent to three standard deviations (3σ) of the "even" intervals, and $M_O$ is equivalent to 3σ of the "odd" intervals. In other embodiments, the margins may be determined using other methods such as, for example, a different scaling factor of the standard deviations (e.g., two standard deviations, 3.5 standard deviations, etc.), a percentage of the means of the Detected R-R intervals, or preset values determined from statistical analysis, including values determined using artificial intelligence techniques. In embodiments that use 3σ margins in equations (1) and (3) that if satisfied, there should be a 99.7% chance that the "odd" and "even" intervals are different and indicate double counting. If 2σ is used for the margins, there would be a 95% chance the two groups are different. One factor in determining the "scaling" of the standard deviations in some embodiments is a consideration that if the "even" and "odd" Detected R-R intervals are erroneously identified as being different, then equation (5) would be erroneously invoked. In such a case, an erroneously low heart rate would result, which could cause the WCD to deny the patient therapy. But if the criteria are too tight, then WCD might fail to detect T-wave overcounting, which could cause the WCD to initiate the shock delivery process when the patient doesn't need to be shocked.

In embodiments in which HR module 336 is configured with algorithms to detect both T-wave overcounting and bigeminy, the values of the margins are the same for both T-waves and bigeminy detection. In other embodiments, the values of the margins used for bigeminy detection are different from the values of the margins used in T-wave overcounting detection.

In some embodiments, HR module 336 implements a threshold (TH) used as part of the determination of whether a difference in the EVEN MEAN and the ODD MEAN is due to bigeminy. In some embodiments HR module 336 is configured with criteria or rules to determine whether the "even" and "odd" intervals are substantially different. For example, some embodiments of HR module 336 are configured to compare the EVEN MEAN to the ODD MEAN and to detect that a bigeminy rhythm exists if both Equation (6) and Equation (7) are satisfied, or if both Equation (8) and Equation (9) are satisfied:

$$(\text{EVEN MEAN}+M_E)<(\text{ODD MEAN}-M_O) \quad (6)$$

and $$(\text{EVEN MEAN})\geq TH \quad (7)$$

or $$(\text{ODD MEAN}+M_O)<(\text{EVEN MEAN}-M_E) \quad (8)$$

and $$(\text{ODD MEAN})\geq TH \quad (9)$$

Similar to embodiments for detecting T-wave overcounting, in embodiments the value of TH in equations (7) and (9) is set as a function of the refractory period that is a parameter of the QRS detection algorithm. In some embodiments, the value of TH is set to about twice the refractory period or 240 ms, but in other embodiments the value of TH can range from 100 to 300 ms. Because the abnormal heartbeat of bigeminy rhythms typically occur after the refractory period, equations (7) and (9) can serve to confirm that EVEN MEAN or ODD MEAN corresponds to an average duration of the shorter interval is longer than the refractory period so that the following heartbeat begins after the refractory period and, therefore, bigeminy has been detected. Stated another way, if the shorter interval is very short it is deemed to result from large T-waves being detected as an R-wave, and if not then it is deemed to result from bigeminy.

In response to HR module 336 detecting bigeminy, some embodiments of HR module 336 are configured to output an indication or alert that bigeminy has been detected. This notification can be received by other modules of processor 230 and provided to the patient via interface 280, stored in memory 238, and/or communicated to other devices via communication module 290. In addition, some embodiments of HR module 336 are further configured to determine EVEN MEAN and ODD MEAN in seconds and to output HR 333 in beats per minute according to equation (10).

$$HR=120/(\text{EVEN MEAN}+\text{ODD MEAN}) \quad (10)$$

In some embodiments, HR 333 is substantially equal to the HR according to Equation (10) with rounding to the nearest integer or other selected accuracy.

On the other hand, if bigeminy is not detected, embodiments of HR module 336 are configured to treat both "even" and "odd" intervals as normal R-R intervals as described above in conjunction with FIG. 5A. In some embodiments, HR module 366 will output HR 333 by determining the inverse of the mean of all the intervals used to determine EVEN MEAN and ODD MEAN. In some embodiments, HR 333 is substantially equal to the HR according inverse of the mean of all such intervals with rounding to the nearest integer or other selected accuracy.

The devices and/or systems mentioned in this document perform functions, processes and/or methods. These functions, processes and/or methods may be implemented by one or more devices that include logic circuitry. Such a device can be alternately called a computer, a processor and so on. It may be a standalone device or computer, such as a general-purpose computer, special purpose computer, or part of a device that has one or more additional functions. The logic circuitry may include a processor and non-transitory computer-readable storage media, such as memories, of the type described above in this document. Often, for the sake of convenience, it is preferred to implement and describe a program as various interconnected distinct software modules or features. These, along with data are individually and also collectively known as software. In some instances, software is combined with hardware, in a mix called firmware.

This detailed description includes flow charts, algorithms, and symbolic representations of program operations, which according to some embodiments may be implemented within at least one computer readable medium. Embodiments of flow charts described herein may implement methods, programs, software, firmware, etc.

Figure 6:
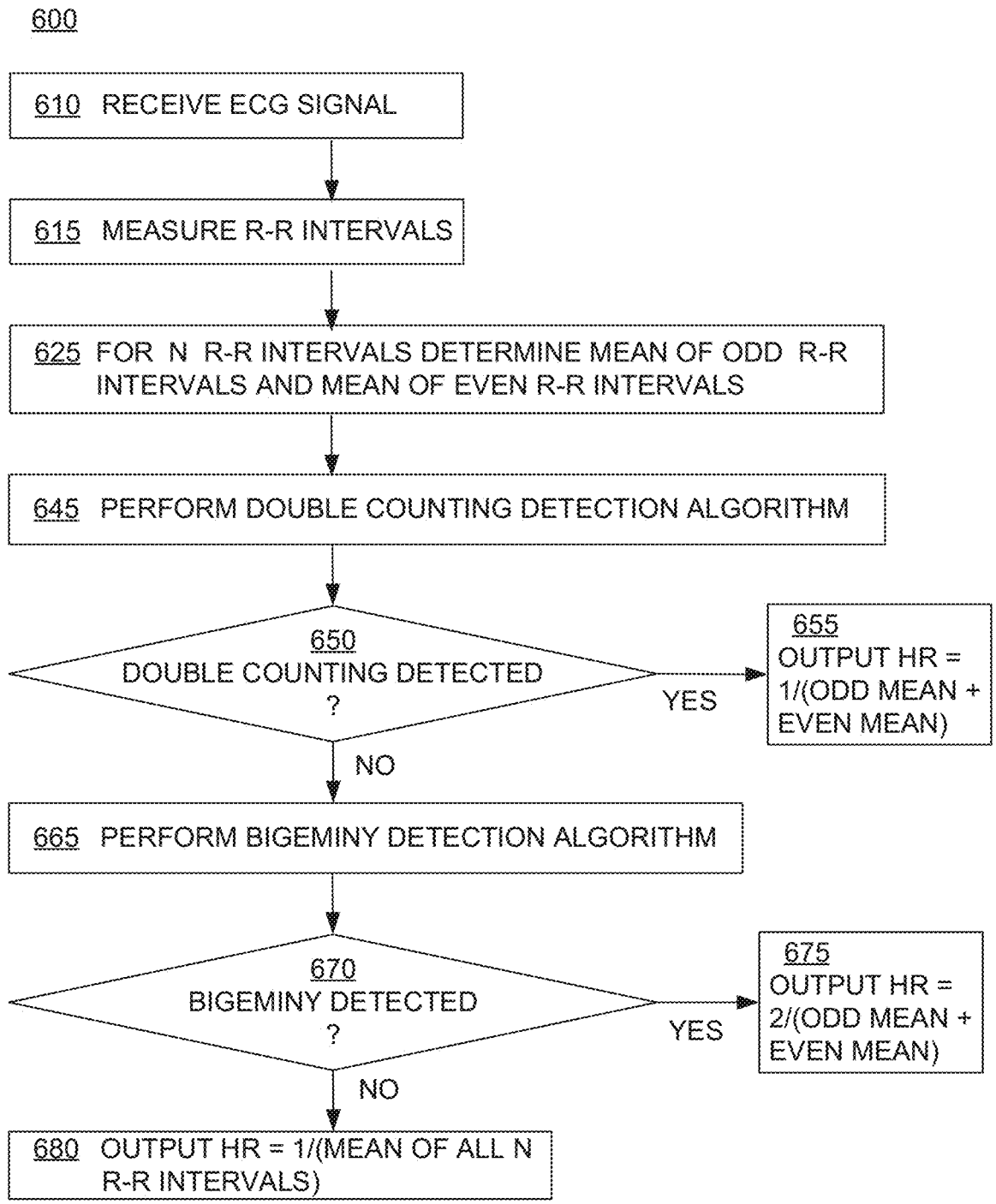
FIG. 6 is a flow chart illustrating methods of calculating a HR with reduced overcounting, according to embodiments.

FIG. 6 is a flow chart illustrating embodiments of a method 600 for determining a user's HR with reduced overcounting. Method 600 may be performed by software, programs, firmware, etc. used by computers, processors, controllers, or devices such as defibrillators (including external and internal defibrillators), heart rate monitors, pacemakers, etc. that incorporate computers, processors, controllers, etc. In some embodiments, method 600 is performed by WCDs when worn by a patient, such as the embodiments of WCDs described above in conjunction with FIGS. 1-5.

In an operation 610, a portion of an ECG is received. In some embodiments, operation 610 performed by one or more components of a WCD such as, for example, processor 230 (FIGS. 2 and 3) receiving ECG signals via ECG electrodes 209 and sensor port 219. In some embodiments, the WCD uses a segment-based Shock Advisory Algorithm and the portion of the ECG signal is a segment of length 4.8 seconds. In other embodiments, the segment length can range from 2.5 to 15 seconds.

In an operation 615, the R-R intervals in the received ECG portion are measured. In some embodiments, the R-R intervals are measured by a processor or HR monitor such as, for example, processor 230 with as HR module 336 (FIG. 3). The R-R intervals are measured in some embodiments by detecting peaks exceeding a predetermined or preset amplitude in the received ECG portion, which are deemed to be R-waves. But as previously described, these peaks may be caused by large T-waves or by abnormal bigeminy contractions rather than R-waves of a normal heartbeat. Thus, in some patients the measured R-R intervals may be erroneous as shown in FIG. 4B or 5B.

In an operation 625, for N (where N is a positive integer) measured R-R intervals, a mean of the "odd" R-R interval measurements and a mean of the "even" R-R interval measures are determined. In some embodiments, N is equal to 10 R-R interval measurements. In other embodiments, N can range from 5 to 20. In some embodiments, N is equal to the number of R-R interval measurements that occur in the most recently received 10 seconds of ECG signal. In other embodiments, N can range from 5 to 20 seconds. In some embodiments N is equal to the number of R-R interval measurements in the most recent segment or the 5 most recent segments. In embodiments, operation 625 is performed by a processor such as, for example, processor 230 and HR module 336 (FIG. 3).

In an operation 645, a double counting algorithm is performed. In some embodiments, operation 645 is performed by a processor or HR monitor such as, for example, processor 230 and HR module 336 (FIG. 3). Embodiments of the double counting algorithm use the means of the "odd" and "even" intervals determined in operation 625, as described below in conjunction with FIG. 7. In some embodiments, the algorithm is based on previously described Equations (1)-(4) used to detect R-R interval overcounting in patients with large T-wave rhythms.

In embodiments, method 600 performs an operation 650 to analyze one or more results of operation 645. In some embodiments, operation 650 is performed by a processor or HR monitor such as, for example, processor 230 with as HR module 336 (FIG. 3). If a result of operation 645 is that double counting is detected, operation 650 proceeds to an operation 655.

In embodiments, operation 655 is performed to determine the user's HR without inaccuracies due to R-R interval double counting. In some embodiments, operation 655 is performed by a processor or HR monitor such as, for example, processor 230 with as HR module 336 (FIG. 3). In embodiments, the HR is calculated using Equation (6), described above.

However, if in operation 645 double counting is not detected, in some embodiments operation 650 proceeds to an operation 665 to perform an algorithm to determine whether the patient has a bigeminy rhythm. In some embodiments, operation 665 is performed by a processor or HR monitor such as, for example, processor 230 and HR module 336 (FIG. 3). Embodiments of the bigeminy algorithm use the means of the "odd" and "even" intervals determined in operation 625, as described below in conjunction with FIG. 8. In some embodiments, the bigeminy algorithm is based on previously described Equations (6)-(9).

In embodiments, method 600 performs an operation 670 to analyze one or more results of operation 665. In some embodiments, operation 670 is performed by a processor or HR monitor such as, for example, processor 230 with as HR module 336 (FIG. 3). If a result of operation 665 is that bigeminy is detected, operation 670 proceeds to an operation 675.

In embodiments, operation 675 is performed to determine the user's HR without inaccuracies due to bigeminy. In some embodiments, operation 675 is performed by a processor or HR monitor such as, for example, processor 230 with as HR module 336 (FIG. 3). In embodiments, the HR is calculated using Equation (10), described above.

However, if operations 665 determines that the user does not have bigeminy, operation 680 is performed to determine the user's HR. In some embodiments, operation 680 is performed by a processor or HR monitor such as, for example, processor 230 and HR module 336 (FIG. 3). Because at this point neither double counting nor bigeminy has been detected, the user's R-R intervals are deemed "normal" and the user's HR can be determined in a conventional manner. For example, in some embodiments the HR is determined by taking the inverse of the mean of all of the R-R intervals measured in operation 615 described above.

Other Embodiments of Method 600

In some embodiments of method 600, operations 645, 650 and 655 are not performed (i.e., method 600 does not detect double counting). Rather, after operation 625, method 600 proceeds to operation 670 to determine whether the user has a bigeminy rhythm.

Conversely, in some other embodiments of method 600, operations 665, 670 and 675 are skipped (i.e., method 600 does not detect bigeminy). So, if double counting is not detected in operation 645, method 600 proceeds to operation 680 to determine the user's HR.

Further, in some embodiments of method 600, operation 670 and 675 are performed before operations 650 and 655 so that bigeminy is tested before double counting.

Figure 7:
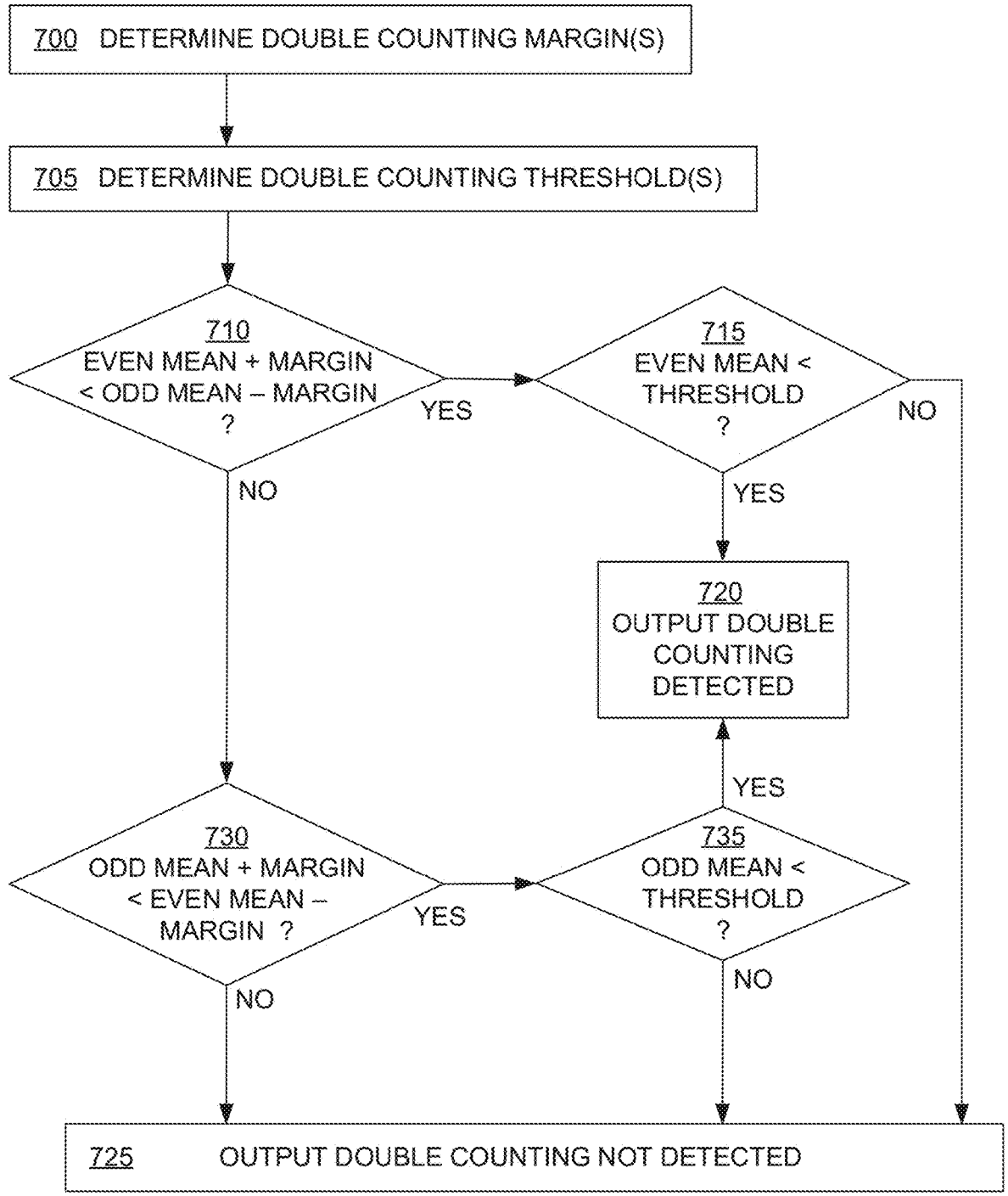
FIG. 7 is a flow chart illustrating methods of detecting double counting, for example caused by large T-waves, according to embodiments.

Still further, in some embodiments, method 600 is configurable into one of several modes, including a mode to detect double counting, a mode to detect bigeminy, and a mode to detect both bigeminy and double counting. In embodiments, the processor or device that can perform method 600 is configured into a selected mode by a clinician, or the user, or FIG. 7 is a flow chart illustrating methods of detecting double counting in operation 645 (FIG. 6), according to embodiments. Operation 645 may be performed by software, programs, firmware, etc. used by computers, processors, controllers, or devices such as defibrillators (including external and internal defibrillators), heart rate monitors, pacemakers, etc. that incorporate computers, processors, controllers, etc. In some embodiments, method 600 is performed by WCDs when worn by a patient, such as the embodiments of WCDs described above in conjunction with FIGS. 1-5.

In an operation 700, one or more double counting margins are determined. As previously described, double counting margins are used in embodiments in determining whether the ODD MEAN and EVEN MEAN are different enough to indicate double counting has occurred. In some embodiments, the margin(s) are the margins $M_E$ and $M_O$ described above for use in Equations (1) and (3). In embodiments, this operation and the rest of the operations shown in FIG. 7 are performed by a processor or HR monitor such as, for example, processor 230 with as HR module 336 (FIG. 3).

In an operation 705, one or more double counting thresholds are determined. As previously described, a double counting threshold is used as part of the determination of whether a difference in the EVEN MEAN and the ODD MEAN is due to T-wave double counting. In some embodiments, the threshold(s) is the threshold TH described above for use in Equations (2) and (4). In a further refinement, there may be two thresholds to implement hysteresis.

In some embodiments, operation 700 is performed after or concurrently (e.g., using multiple or multi-core processors) with operation 705.

In an operation 710, the value of EVEN MEAN plus a margin determined in operation 700 is compared to the value of ODD MEAN minus a margin determined in operation 700. In some embodiments, these margins are the margins $M_E$ and $M_O$ described above for use in Equation (1).

If in operation 710 it is determined that the value of EVEN MEAN plus margin is less than the value of ODD MEAN minus margin, then an operation 715 is performed. In operation 715, EVEN MEAN is then compared to the threshold determined in operation 705 to determine if the mean is less than the threshold (i.e., the short interval is short enough to indicate double counting). In some embodiments, the threshold is TH described above for use in Equation (2).

If in operation 715 it is determined that EVEN MEAN is less than the threshold, then an operation 720 is performed. In operation 720, an output is provided to indicate that double counting has been detected and operation 645 is exited to proceed to operation 650 (FIG. 6).

However, if it is determined in operation 715 that EVEN MEAN is greater than or equal to the threshold, then an operation 725 is performed. in which an output is provided to indicate that double counting has not been detected and operation 645 is exited to proceed to operation 650 (FIG. 6).

Referring back to operation 710, if it is determined that the value of EVEN MEAN plus margin is not less than the value of ODD MEAN minus margin, then an operation 730 is performed.

In operation 730, the value of ODD MEAN plus a margin determined in operation 700 is compared to the value of EVEN MEAN minus a margin determined in operation 700. In some embodiments, these margins are the margins $M_E$ and $M_O$ described above for use in Equation (3).

If in operation 730 it is determined that the value of ODD MEAN plus margin is less than the value of EVEN MEAN minus margin, then an operation 735 is performed. In operation 735, ODD MEAN is then compared to the threshold determined in operation 705 to determine if the mean is less than the threshold (i.e., the short interval is short enough to indicate double counting). In some embodiments, the threshold is TH described above for use in Equation (4).

If in operation 735 it is determined that ODD MEAN is less than the threshold, then operation 735 proceeds to operation 720 to output that double counting has been detected and exit operation 645, as previously described.

However, if it is determined in operation 735 that ODD MEAN is greater than or equal to the threshold, then operation 725 is performed and operation 645 is exited, as previously described.

In some embodiments, operations 730 and 735 are performed before or concurrently with operations 710 and 715 with appropriate changes in the flow in a way that satisfies Equations (1)-(4). Further, in some embodiments, operation 715 is performed before or concurrently with operation 710, and in other embodiments operation 735 is performed before or concurrently with operation 730, with appropriate changes in the flow to operations 720 and 725.

Figure 8:
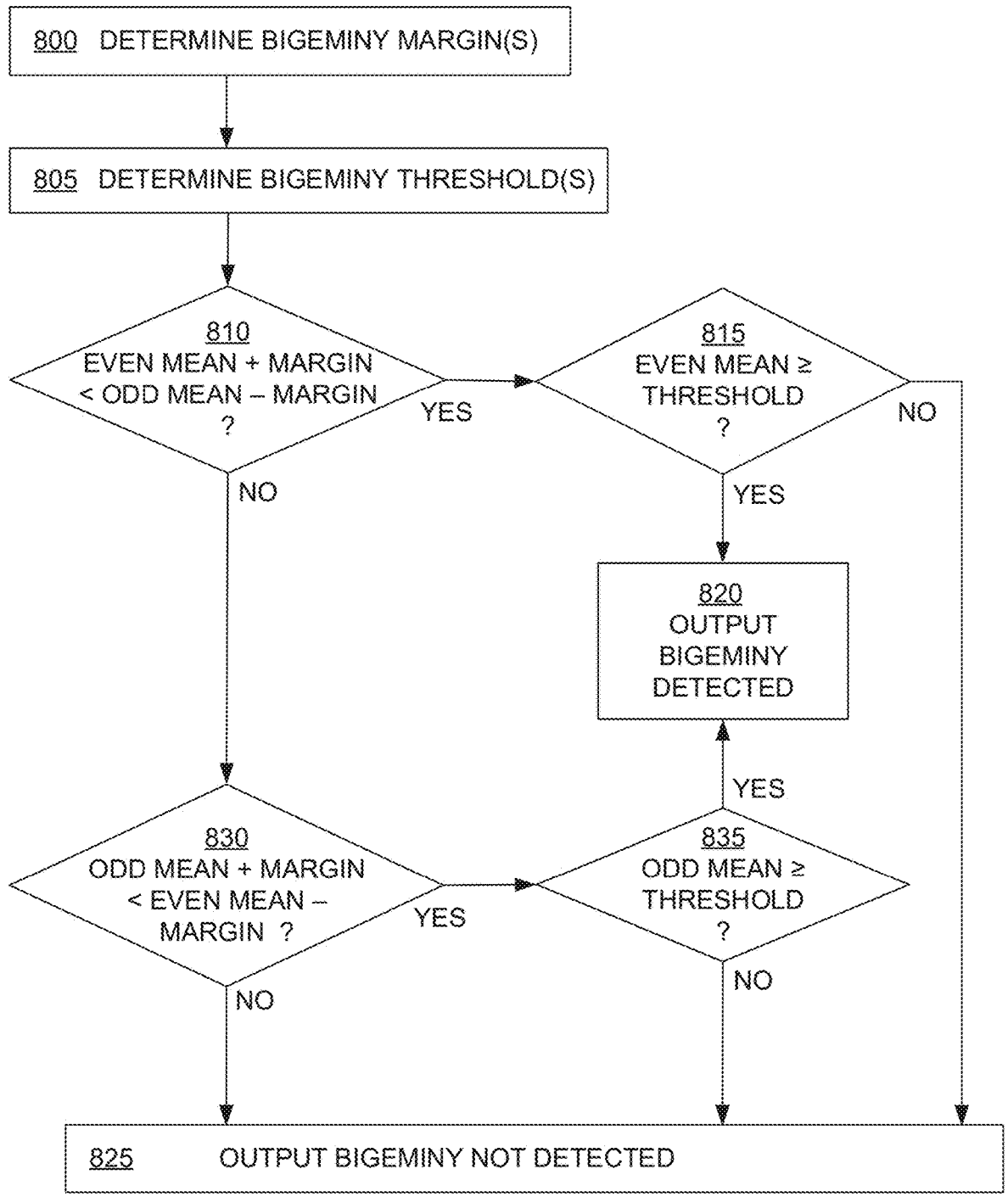
FIG. 8 is a flow chart illustrating methods of detecting bigeminy, according to embodiments.

FIG. 8 is a flow chart illustrating methods of detecting bigeminy in operation 665 (FIG. 6), according to embodiments. Operation 665 may be performed by software, programs, firmware, etc. used by computers, processors, controllers, or devices such as defibrillators (including external and internal defibrillators), heart rate monitors, pacemakers, etc. that incorporate computers, processors, controllers, etc. In some embodiments, method 600 is performed by WCDs when worn by a patient, such as the embodiments of WCDs described above in conjunction with FIGS. 1-5.

In an operation 800, one or more bigeminy margins are determined. As previously described, bigeminy margins are used in embodiments in determining whether the ODD MEAN and EVEN MEAN are different enough to indicate bigeminy has occurred. In some embodiments, the bigeminy margins are the same as the double counting margins determined in operation 700 (FIG. 7), while in other embodiments they are different. In some embodiments, the margin (s) are the margins $M_E$ and $M_O$ described above for use in Equations (6) and (8). In embodiments, this operation and the rest of the operations shown in FIG. 8 are performed by a processor or HR monitor such as, for example, processor 230 with as HR module 336 (FIG. 3).

In an operation 805, one or more thresholds are determined. As previously described, a threshold is used as part of the determination of whether a difference in the EVEN MEAN and the ODD MEAN is due to bigeminy. In some embodiments, the bigeminy threshold(s) are the same as the double counting threshold(s) determined in operation 700 (FIG. 7), while in other embodiments they are different. In some embodiments, the threshold(s) is the threshold TH described above for use in Equations (7) and (9). In a further refinement, there may be two thresholds to implement hysteresis.

In some embodiments, operation 800 is performed after or concurrently (e.g., using multiple or multi-core processors) with operation 805.

In an operation 810, the value of EVEN MEAN plus a margin determined in operation 800 is compared to the value of ODD MEAN minus a margin determined in operation 800. In some embodiments, these margins are the margins $M_E$ and $M_O$ described above for use in Equation (6).

If in operation 810 it is determined that the value of EVEN MEAN plus margin is less than the value of ODD MEAN minus margin, then an operation 815 is performed. In operation 815, EVEN MEAN is then compared to the threshold determined in operation 705 to determine if the mean is greater than or equal to the threshold (i.e., the short interval is long to indicate bigeminy). In some embodiments, the threshold is equal to TH described above for use in Equation (7).

If in operation 815 it is determined that EVEN MEAN is greater than or equal to the threshold, then an operation 820 is performed. In operation 820, an output is provided to indicate that bigeminy has been detected and operation 665 is exited to proceed to operation 670 (FIG. 6).

However, if it is determined in operation 815 that EVEN MEAN is less than the threshold, then an operation 825 is performed. in which an output is provided to indicate that bigeminy has not been detected and operation 665 is exited to proceed to operation 670 (FIG. 6).

Referring back to operation 810, if it is determined that the value of EVEN MEAN plus margin is not less than the value of ODD MEAN minus margin, then an operation 830 is performed.

In operation 830, the value of ODD MEAN plus a margin determined in operation 800 is compared to the value of EVEN MEAN minus a margin determined in operation 800. In some embodiments, these margins are the margins $M_E$ and $M_O$ described above for use in Equation (8).

If in operation 830 it is determined that the value of ODD MEAN plus margin is less than the value of EVEN MEAN minus margin, then an operation 835 is performed. In operation 835, ODD MEAN is then compared to the threshold determined in operation 805 to determine if the mean is greater than or equal to the threshold (i.e., the short interval is long enough to indicate bigeminy). In some embodiments, the threshold is equal to TH described above for use in Equation (9).

If in operation 835 it is determined that ODD MEAN is greater than or equal to the threshold, then operation 835 proceeds to operation 820 to output that bigeminy has been detected and exit operation 665, as previously described.

However, if it is determined in operation 835 that ODD MEAN is less than the threshold, then operation 825 is performed and operation 665 is exited, as previously described.

In some embodiments, operations 830 and 835 are performed before or concurrently with operations 810 and 815 with appropriate changes in the flow in a way that satisfies Equations (6)-(9). Further, in some embodiments, operation 815 is performed before or concurrently with operation 810, and in other embodiments operation 835 is performed before or concurrently with operation 830, with appropriate changes in the flow to operations 820 and 825.

In the methods described above, each operation can be performed as an affirmative act or operation of doing, or causing to happen, the features of the operation. Such doing or causing to happen can be by the whole system or device, or just one or more components of it. It will be recognized after review of the present disclosure that the described methods and the operations may be implemented in a number of ways, including using systems, devices and implementations described above. In addition, the order of operations is not constrained to what is shown, and different orders may be possible according to different embodiments. Examples of such alternate orderings may include overlapping, interleaved, interrupted, reordered, incremental, preparatory, supplemental, simultaneous, reverse, or other variant orderings, unless context dictates otherwise. Moreover, in certain embodiments, new operations may be added, or individual operations may be modified or deleted. The added operations can be, for example, from what is mentioned while primarily describing a different system, apparatus, device or method.

A person skilled in the art will be able to practice the present invention in view of this description, which is to be taken as a whole. Details have been included to provide a thorough understanding. In other instances, well-known aspects have not been described, in order to not obscure unnecessarily this description.

Some technologies or techniques described in this document may be known. Even then, however, it does not necessarily follow that it is known to apply such technologies or techniques as described in this document, or for the purposes described in this document.

This description includes one or more examples, but this fact does not limit how the invention may be practiced. Indeed, examples, instances, versions or embodiments of the invention may be practiced according to what is described, or yet differently, and also in conjunction with other present or future technologies. Other such embodiments include combinations and sub-combinations of features described herein, including for example, embodiments that are equivalent to the following: providing or applying a feature in a different order than in a described embodiment; extracting an individual feature from one embodiment and inserting such feature into another embodiment; removing one or more features from an embodiment; or both removing a feature from an embodiment and adding a feature extracted from another embodiment, while providing the features incorporated in such combinations and sub-combinations.

In general, the present disclosure reflects preferred embodiments of the invention. The attentive reader will note, however, that some aspects of the disclosed embodiments extend beyond the scope of the claims. To the respect that the disclosed embodiments indeed extend beyond the scope of the claims, the disclosed embodiments are to be considered supplementary background information and do not constitute definitions of the claimed invention.

In this document, the phrases "constructed to" and/or "configured to" denote one or more actual states of construction and/or configuration that is fundamentally tied to physical characteristics of the element or feature preceding these phrases and, as such, reach well beyond merely describing an intended use. Any such elements or features can be implemented in a number of ways, as will be apparent to a person skilled in the art after reviewing the present disclosure, beyond any examples shown in this document.

Any and all parent, grandparent, great-grandparent, etc. patent applications, whether mentioned in this document or in an Application Data Sheet ("ADS") of this patent application, are hereby incorporated by reference herein as originally disclosed, including any priority claims made in those applications and any material incorporated by reference, to the extent such subject matter is not inconsistent herewith.

In this description a single reference numeral may be used consistently to denote a single item, aspect, component, or process. Moreover, a further effort may have been made in the drafting of this description to use similar though not identical reference numerals to denote other versions or embodiments of an item, aspect, component or process that are identical or at least similar or related. Where made, such a further effort was not required, but was nevertheless made gratuitously so as to accelerate comprehension by the reader. Even where made in this document, such a further effort might not have been made completely consistently for all of the versions or embodiments that are made possible by this description. Accordingly, the description controls in defining an item, aspect, component or process, rather than its reference numeral. Any similarity in reference numerals may be used to infer a similarity in the text, but not to confuse aspects where the text or other context indicates otherwise.

The claims of this document define certain combinations and subcombinations of elements, features and acts or operations, which are regarded as novel and non-obvious. Additional claims for other such combinations and subcombinations may be presented in this or a related document. These claims are intended to encompass within their scope all changes and modifications that are within the true spirit and scope of the subject matter described herein. The terms used herein, including in the claims, are generally intended as "open" terms. For example, the term "including" should be interpreted as "including but not limited to," the term "having" should be interpreted as "having at least," etc. If a specific number is ascribed to a claim recitation, this number is a minimum but not a maximum unless stated otherwise. For example, where a claim recites "a" component or "an" item, it means that it can have one or more of this component or item.

In construing the claims of this document, the inventor(s) invoke 35 U.S.C. § 112(f) only when the words "means for" or "steps for" are expressly used in the claims. Accordingly, if these words are not used in a claim, then that claim is not intended to be construed by the inventor(s) in accordance with 35 U.S.C. § 112(f).

What is claimed is:

1. A wearable cardioverter defibrillator (WCD) system, comprising:
   a support structure configured to be worn by a patient;
   an energy storage module configured to store an electrical charge;
   a discharge circuit coupled to the energy storage module;
   one or more sensors configured to sense an Electrocardiogram (ECG) signal of the patient while the patient is wearing the support structure; and
   a processor having a memory, wherein the memory is configured with:
      classification criteria to classify the ECG signal into one of a plurality of ECG rhythm types, and
      for each of the plurality of ECG rhythm types, a corresponding set of operations to determine a heart rate of the patient, wherein each set of the corresponding sets of operations is different from every other set of the corresponding sets of operations,
   wherein the processor is configured to:
      receive the ECG signal from the one or more sensors,
      analyze the received ECG signal, using the classification criteria, to identify an ECG rhythm type of the plurality of ECG rhythm types into which the received ECG signal is classified, wherein, to identify the ECG rhythm type, the processor is configured to:
         apply a first margin of one or more margins to a combination of even measured intervals using a first operator, and a second margin of the one or more margins to a combination of odd measured intervals using a second operator, wherein the combination of even measured intervals and the combination of odd measured intervals are obtained from the received ECG signal, and
         after the application, compare the combination of even measured intervals to the combination of odd measured intervals to identify the ECG rhythm type, and
      determine the heart rate of the patient using the set of operations corresponding to the identified ECG rhythm type.

2. The WCD system of claim 1, wherein the plurality of ECG rhythm types comprises at least one of a default type, a double-counting type, or a bigeminy type.

3. The WCD system of claim 1, wherein, to identify the ECG rhythm type, the processor is configured to determine a pattern of measured intervals based on the comparison, and wherein each measured interval of the measured intervals is substantially equivalent to the time between successive detected peaks.

4. The WCD system of claim 3, wherein the time between successive detected peaks comprises an R-R interval of the received ECG signal.

5. The WCD system of claim 1, wherein, to compare the combination of even measured intervals to the combination of odd measured intervals, the processor is configured to determine whether a mean of the even measured intervals is substantially different from a mean of the odd measured intervals using pattern criteria.

6. The WCD system of claim 5, wherein when the mean of the even measured intervals is substantially different from the mean of the odd measured intervals, the processor is further configured to indicate that bigeminy is present.

7. The WCD system of claim 6, wherein the processor is further configured to adjust the corresponding set of operations to determine the heart rate of the patient according to the indication that bigeminy is present.

8. The WCD system of claim 1, wherein the plurality of ECG rhythm types comprises a default type, a double-counting type, and a bigeminy type.

9. The WCD system of claim 1, wherein each of the first operator and the second operator includes one of an addition operator or a subtraction operator.

10. The WCD system of claim 1, wherein to identify the ECG rhythm type, the processor is further configured to:
    compare a mean of the even measured intervals or a mean of the odd measured intervals with a threshold, based on a result of the comparison of the combination of even measured intervals to the combination of odd measured intervals.

11. The WCD system of claim 10, wherein in response to a determination that the mean of the even measured intervals or the mean of the odd measured intervals is less than the threshold, the ECG rhythm type is identified as double-counting.

12. A heart rate monitor system, comprising:
    one or more sensors configured to sense an Electrocardiogram (ECG) signal of a patient; and
    a processor having a memory, wherein the memory is configured with:
       classification criteria to classify the ECG signal into one of a plurality of ECG rhythm types, and
       for each of the plurality of ECG rhythm types, a corresponding set of operations to determine a heart rate of the patient, wherein each set of the corresponding sets of operations is different from every other set of the corresponding sets of operations, and
    wherein the processor is configured to:
       receive the ECG signal from the one or more sensors,
       analyze the received ECG signal, using the classification criteria, to identify an ECG rhythm type of the plurality of ECG rhythm types into which the received ECG signal is classified, wherein, to identify the ECG rhythm type, the processor is configured to:
          determine an odd mean of odd measured intervals and an even mean of even measured intervals, wherein the odd measured intervals and the even measured intervals are obtained from the received ECG signal,
          determine one or more double counting margins,
          apply a first margin of the one or more double counting margins to the odd mean using a first operator, and a second margin of the one or more double counting margins to the even mean using a second operator,
          upon the application, compare the odd mean with the even mean to determine a pattern of measured intervals in the received ECG signal, and identify the ECG rhythm type as a double counting type based on the determined pattern, and
determine the heart rate of the patient using the set of operations corresponding to the identified ECG rhythm type.

13. The heart rate monitor system of claim 12, wherein the plurality of ECG rhythm types comprises at least one of a default type, a double counting type, or a bigeminy type.

14. The heart rate monitor system of claim 12, wherein each measured interval of the measured intervals is substantially equivalent to the time between successive detected peaks.

15. The heart rate monitor system of claim 14, wherein the time between successive detected peaks comprises an R-R interval of the received ECG signal.

16. The heart rate monitor system of claim 12, wherein, to compare a combination of the even measured intervals to a combination of the odd measured intervals, the processor is configured to determine whether the even mean of the even measured intervals is substantially different from the odd mean of the odd measured using pattern criteria.

17. The heart rate monitor system of claim 16, wherein when the even mean of the even measured intervals is substantially different from the odd mean of the odd measured intervals, the processor is further configured to indicate that bigeminy is present.

18. The heart rate monitor system of claim 17, wherein the processor is further configured to adjust the corresponding set of operations to determine the heart rate of the patient according to the indication that bigeminy is present.

* * * * *